United States Patent [19]

Ward et al.

[11] Patent Number: 4,548,948

[45] Date of Patent: Oct. 22, 1985

[54] ANTI-INFLAMMATORY AND ANALGESIC BENZOTHIOPHENE AND BENZAFURAN DERIVATIVES, COMPOSITIONS, AND METHOD OF USE THEREFOR

[75] Inventors: Robert W. Ward, Harlow; Stephen A. Smith, Bishops Stortford; Roger E. Markwell, Great Dunmow, all of England

[73] Assignee: Beecham Group p.l.c., Middlesex, England

[21] Appl. No.: 581,440

[22] Filed: Feb. 17, 1984

[30] Foreign Application Priority Data

Feb. 19, 1983 [GB] United Kingdom ............ 8304647
Jul. 27, 1983 [GB] United Kingdom ............ 8320182
Nov. 5, 1983 [GB] United Kingdom ............ 8329607

[51] Int. Cl.⁴ ............ A61K 31/34; A61K 31/38; A61K 31/40; C07D 333/38
[52] U.S. Cl. ............ 514/422; 514/423; 514/427; 514/428; 514/443; 514/444; 514/448; 514/461; 548/517; 549/49; 549/53; 549/54; 549/60; 549/462; 549/469
[58] Field of Search ............ 424/274, 275, 278, 285; 548/517; 549/49, 53, 54, 60; 549/462, 469

[56] References Cited

U.S. PATENT DOCUMENTS 3,923,866 12/1975 Sawa et al. ............ 260/469
3,953,500 4/1976 Noguchi et al. ............ 260/517
4,087,539 5/1978 Muchowski et al. ............ 424/274
4,087,542 5/1978 Cragoe, Jr. et al. ............ 424/275
4,089,969 5/1978 Muchowski et al. ............ 424/274
4,097,579 1/1978 Muchowski et al. ............ 424/274

FOREIGN PATENT DOCUMENTS 865247 9/1978 Belgium ............ 424/275

0000649 2/1979 European Pat. Off. ............ 424/275

OTHER PUBLICATIONS

Taylor et al., J. Amer. Chem. Soc., 1976, 98, p. 6750.

Primary Examiner—Henry R. Jiles
Assistant Examiner—J. G. Mullins
Attorney, Agent, or Firm—James F. Haley, Jr.; Paul H. Ginsburg; Irene J. Frangos

[57] ABSTRACT

Compounds of formula (I):

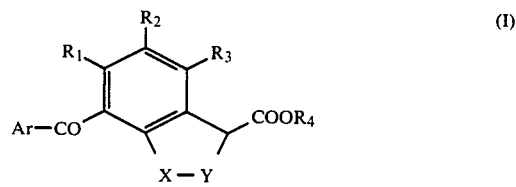

wherein:

Ar is phenyl optionally substituted in the o-, m- or p-position by $C_{1-4}$ alkyl, $C_{1-4}$ alkoxy, trifluoromethyl, bromo, chloro or fluoro,
  pyrryl optionally N-substituted by $C_{1-4}$ alkyl,
  2-furyl or 2-thienyl either optionally substituted in the 3-, 4- or 5-position by methyl, chloro or bromo, or 3-furyl or 3-thienyl;

X is oxygen, sulphur, sulphoxide or sulphone, Y is methylene, $R_1$ and $R_3$ are hydrogen or $C_{1-4}$ alkyl, and $R_2$ is hydrogen, $C_{1-4}$ alkyl, fluoro, chloro or bromo, or X is methylene, Y is oxygen, $R_1$ and $R_3$ are both hydrogen, and $R_2$ is hydrogen, fluoro, chloro or bromo; and $R_4$ is hydrogen or $C_{1-4}$ alkyl, or a salt thereof, have analgesic and/or anti-inflammatory activity.

13 Claims, No Drawings

ANTI-INFLAMMATORY AND ANALGESIC BENZOTHIOPHENE AND BENZAFURAN DERIVATIVES, COMPOSITIONS, AND METHOD OF USE THEREFOR

This invention relates to novel compounds having pharmacological activity, to processes of their preparation, to pharmaceutical compositions containing them, and to their use in the treatment of mammals.

U.S. Pat. Nos. 4,087,539, 4,089,969 and 4,097,579, European Patent Publication No. 649 and Belgian Pat. No. 865,247 disclose pyrrolopyrrole derivatives that are described as having various pharmacological activities including anti-inflammatory activity and analgesic activity.

U.S. Pat. Nos. 3,923,866 and 3,953,500 disclose indan derivatives that are described as being useful as anti-pyretics, analgesics and anti-inflammatory agents.

Another class of compounds has now been discovered which compounds are dihydrobenzofuran, dihydroisobenzofuran, dihydrobenzothiophene, dihydrobenzothiophene-1-oxide or dihydrobenzothiophene-1,1-dioxide, carboxylic acids, esters and salts, the benzo moiety being optionally substituted by a benzoyl, pyrrolyl, thienoyl or a furanoyl group. Such compounds, moreover, have been discovered to have analgesic activity and/or anti-inflammatory activity.

Accordingly, the present invention provides a compound of formula (I):

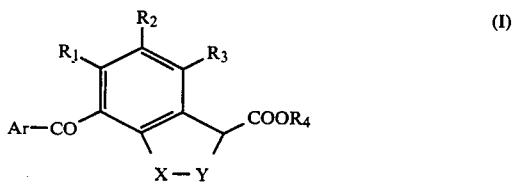

wherein:

Ar is phenyl optionally substituted in the o-, m- or p-position by $C_{1-4}$ alkyl, $C_{1-4}$ alkoxy, trifluoromethyl, bromo, chloro or fluoro,
  pyrryl optionally N-substituted by $C_{1-4}$ alkyl,
  2-furyl or 2-thienyl either optionally substituted in the 3-, 4- or 5-position by methyl, chloro or bromo, or 3-furyl or 3-thienyl;
X is oxygen, sulphur, sulphoxide or sulphone, Y is methylene, $R_1$ and $R_3$ are hydrogen or $C_{1-4}$ alkyl, and $R_2$ is hydrogen, $C_{1-4}$ alkyl, fluoro, chloro or bromo, or X is methylene, Y is oxygen, $R_1$ and $R_3$ are both hydrogen, and $R_2$ is hydrogen, fluoro, chloro or bromo; and
$R_4$ is hydrogen or $C_{1-4}$ alkyl, or a salt thereof.

Preferably, Ar is phenyl optionally substituted in the o-, m- or p-position by $C_{1-4}$ alkyl, $C_{1-4}$ alkoxy, trifluoromethyl, bromo, chloro or fluoro. In particular, Ar is unsubstituted phenyl or p-chlorophenyl.

There are three main sub-groups of compounds that are comprised by the definition of the compounds of formula (I) and these are the compounds containing:
(i) a dihydrobenzofuran moiety, i.e. wherein X is oxygen and Y is methylene;
(ii) a dihydrobenzothiophene, dihydrobenzothiophene-1-oxide or dihydrobenzothiophene-1,1-dioxide moiety, wherein X is sulphur, sulphoxide or sulphone and Y is methylene; and
(iii) a dihydroisobenzofuran moiety, i.e. wherein X is methylene and Y is oxygen.

In relation to the first and second sub-groups of compounds of formula (I), it is preferred that $R_1$ and $R_3$ are both hydrogen or methyl, in particular both hydrogen.

In relation to all three sub-groups of compounds of formula (I), it is preferred that $R_2$ is hydrogen, fluoro or chloro, in particular hydrogen or chloro.

Of the compounds of formula (I), the compounds containing a dihydrobenzofuran moiety or dihydrobenzothiophene moiety are the most preferred.

When $R_4$ is $C_{1-4}$ alkyl, preferred examples include methyl, ethyl and isopropyl. It is preferred, however, that $R_4$ is hydrogen.

A preferred sub-class of salts of a compound of formula (I) is pharmaceutically acceptable salts, examples of which include alkali metal salts, such as potassium and sodium salts, alkaline earth metal salts, such as calcium and magnesium salts, and salts derived from amines, such as tris(hydroxymethyl)aminomethane and 2-amino-2-methyl-1-propanol.

Particularly preferred compounds falling within the scope of formula (I) are 7-benzoyl-2,3-dihydrobenzofuran-3-carboxylic acid; 7-benzoyl-5-fluoro-2,3-dihydrobenzofuran-3-carboxylic acid; 7-benzoyl-5-chloro-2,3-dihydrobenzofuran-3-carboxylic acid; 7-benzoyl-2,3-dihydrobenzothiophene-3-carboxylic acid; and 7-benzoyl-5-chloro-2,3-dihydrobenzothiophene-3-carboxylic acid; or a pharmaceutically acceptable salt thereof.

The compounds of formula (I) hae a chiral centre and may therefore exist in enantiomeric forms. All such forms, individually or as mixtures, are included within the scope of the invention.

The present invention also provides a process of preparing a compound of formula (I) which comprises, in relation to the first and second sub-groups thereof, as defined hereinbefore, reacting a compound of formula (II):

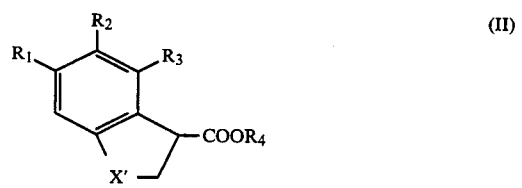

wherein $X^1$ is oxygen, sulphur, sulphoxide or sulphone and $R_1$ to $R_4$ are as defined hereinbefore, with a compound of formula (III):

ArCOL  (III)

wherein Ar is as hereinbefore defined and L is a leaving group; optionally converting $R_2$ or $R_4$ or $X^1$ in the resulting compound of formula (I) into another $R_2$ or $R_4$ or $X^1$ respectively, and optionally forming a salt; or, in relation to the third sub-group of compounds of formula (I), hydrolysing a compound of formula (IV):

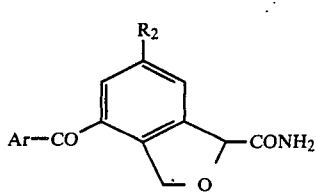

(IV)

wherein Ar and $R_2$ are as hereinbefore defined; and optionally converting $R_2$ or $R_4$ in the resulting compound of formula (I) into another $R_2$ or $R_4$ respectively, and optionally forming a salt.

Preferred examples of a leaving group (L) include chloro, bromo and a group such that the compound of formula (III) is an anhydride.

The reaction between the compounds of formulae (II) and (III) may be carried out under conventional Friedel-Craft conditions, such as in carbon disulphide, in the presence of a Lewis acid, such as aluminium trichloride. In the preparation of a compound of formula (I), wherein $R_2$ is hydrogen, it is preferred that the reaction is carried out with a compound of formula (II), wherein $R_2$ is chloro or bromo, so that no reaction can then occur at this position, and afterwards that the chloro or bromo substituent is converted into hydrogen. In this way, the major product is the desired compound of formula (I) and not a mixture of position isomers. It is also preferred that the reaction is carried out with a compound of formula (II), wherein $R_4$ is $C_{1-4}$ alkyl, in particular ethyl, and afterwards that the alkyl group is optionally converted into hydrogen, as described below.

The hydrolysis of a compound of formula (IV) may be carried out using an aqueous mineral acid.

Examples of an optional conversion of $R_2$ in the resulting compound of formula (I) into another $R_2$ include the optional conversion of bromo or chloro into hydrogen, which, as mentioned above, is a desired conversion if the compound of formula (I) to be prepared is that falling within the first or third sub-group thereof, wherein $R_2$ is hydrogen. Such conversion may be carried out by hydrogenation over a 10% palladium on charcoal catalyst in the presence of a base, such as potassium acetate or triethylamine. The hydrogenation reaction works well for bromo but is a little slower for chloro. In some cases, the Ar—CO— moiety may also be reduced to the alcohol and conditions should be employed that would minimise such reduction occurring. Alternatively, brief treatment of the alcohol with a mild oxidising agent, such as manganese dioxide, would oxidise the alcohol back to the ketone.

Examples of an optional conversion of $R_4$ in the resulting compound of formula (I) into another $R_4$ include the optional conversion of hydrogen into $C_{1-4}$ alkyl and $C_{1-4}$ alkyl into hydrogen. The former conversion may be carried out using conventional $C_{1-4}$ esterifying agents and conditions. For example, the ethyl ester may be prepared by refluxing the carboxylic acid of formula (I) with 2% ethanolic hydrogen chloride solution. The latter conversion may be carried out conventionally, for example, by treating the ester of formula (I) with 5% aqueous sodium hydroxide solution or 10% sodium carbonate solution.

Examples of an optional conversion of $X^1$ in the resulting compound of the third sub-group of compounds of formula (I) into another $X^1$ include the optional conversion of sulphur into sulphoxide or sulphone. The conversion of sulphur into sulphoxide may be carried out with sodium periodate or with one equivalent of m-chloroperbenzoic acid. The conversion of sulphur into sulphone may be carried out with an excess of m-chloroperbenzoic acid.

The optional formation of a salt may be carried out by reacting the compound of formula (I) with conventional salt forming reagents under conventional conditions, for example, by treating the compound of formula (I), wherein $R_4$ is hydrogen, with one equivalent of the alkali metal or alkaline earth metal hydroxide, or with one equivalent of tris(hydroxymethyl)aminomethane in ethanol, or with one equivalent of 2-amino-2-methyl-1-propanol in ether, followed by evaporation to dryness.

The enantiomers of a compound of formula (I) may be obtained in conventional manner by resolution with an optically active base.

The compound of formula (II) may be prepared by reducing a compound of formula (V):

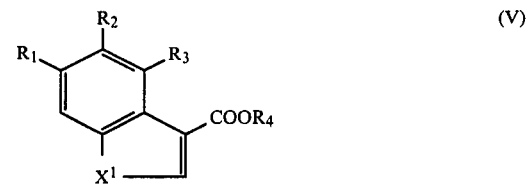

(V)

wherein $X^1$ and $R_1$ to $R_4$ are as defined hereinbefore; and optionally converting $R_2$, $R_4$ or $X^1$ in the resulting compound of formula (II) into another $R_2$, $R_4$ or $X^1$ respectively.

The reduction of a compound of formula (V) may be carried out with a metal and a $C_{1-4}$ alkanol, for example magnesium or sodium with methanol or ethanol. In the case where the reduction is carried out on a compound of formula (V), wherein $R_4$ is hydrogen, it is preferred to use sodium and ethanol as the reducing agent. However, it is even more preferred to carry out the reduction on a compound of formula (V), wherein $R_4$ is methyl, using magnesium and methanol as the reducing agent.

Examples of an optional conversion of $R_2$ in the resulting compound of formula (II) into another $R_2$ include the optional conversion of hydrogen into bromo. In fact, if it is desired to prepare a compound of formula (II), wherein $R_2$ is bromo, then it is preferred to carry out the reduction of a compound of formula (V) with $R_2$ as hydrogen and afterwards to convert the hydrogen atom into bromo. Otherwise, the presence of a bromo substituent during the reduction reaction may lead to some hydrogenolysis of it. Such conversion may be carried out with conventional brominating reagents, for example bromine and acetic acid, and is preferably carried out on a compound of formula (II), wherein $R_4$ is $C_{1-4}$ alkyl, rather than the corresponding compound, wherein $R_4$ is hydrogen.

Examples of an optional conversion of $R_4$ in the resulting compound of formula (II) into another $R_4$ include the optional conversion of hydrogen into $C_{1-4}$ alkyl and, in particular, the optional conversion of $C_{1-4}$ alkyl into another $C_{1-4}$ alkyl. As mentioned previously, it is preferred that, in the reaction between the compounds of formulae (II) and (III), $R_4$ in a compound of formula (II) is ethyl. Therefore, in the preferred case where $R_4$ in the compound of formula (II) resulting from the reduction of a compound of formula (V) is methyl, it is desirale to convert it to ethyl using, for example, an ethanolic solution of sodium ethoxide.

Examples of an optional conversion of $X^1$ in the resulting compound of formula (II) into another $X^1$ include those mentioned hereinbefore.

The compound of formula (V), wherein $X^1$ is oxygen, may be prepared by mono-decarboxylating a compound of formula (VI):

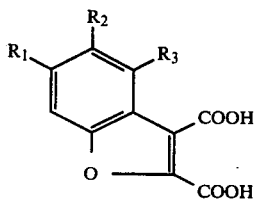

(VI)

wherein $R_1$ to $R_3$ are as defined hereinbefore; and optionally converting $R_4$ in the resulting compound of formula (V) into another $R_4$.

The decarboxylation of a compound of formula (VI) may be carried out simply by heating to a temperature of, for example, 250° to 300° C. The carboxylic group in the 2-position of the compound of formula (VI) preferentially decarboxylates.

Examples of an optional conversion of $R_4$ in the resulting compound of formula (V) into another $R_4$ include the optional conversion of hydrogen into $C_{1-4}$ alkyl. As mentioned previously, it is preferred that, in the reduction of a compound of formula (V), $R_4$ is, preferably, methyl. It is, therefore, preferred that, after the mono-decarboxylation of a compound of formula (VI), the hydrogen atom for $R_4$ in the resulting compound of formula (V) is converted into methyl. Such conversion may be carried out by first converting the free acid to the acid chloride by reaction with, for example, thionyl chloride, and then by converting the acid chloride to the methyl ester by reaction with, for example, methanol in the presence of a base, such as triethylamine.

The compound of formula (VI) may be prepared by hydrolysis of a compound of formula (VII):

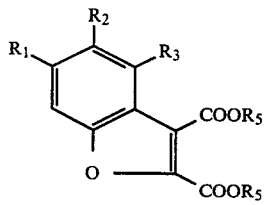

(VII)

wherein $R_1$ to $R_3$ are as defined hereinbefore and $R_5$ is $C_{1-4}$ alkyl, such as ethyl.

The hydrolysis of a compound of formula (VII) may be carried out conventionally with, for example, an aqueous solution of sodium hydroxide.

The compound of formula (VII) may be prepared by dehydrating and cyclising a compound of formula (VIII):

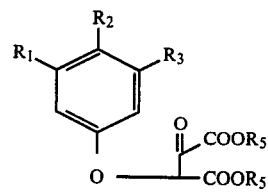

(VIII)

wherein $R_1$ to $R_3$ and $R_5$ are as defined hereinbefore.

The dehydration and cyclisation of a compound of formula (VIII) may be carried out with, for example, concentrated sulphuric acid at room temperature.

The compound of formula (VIII) may be prepared by reacting a compound of formula (IX):

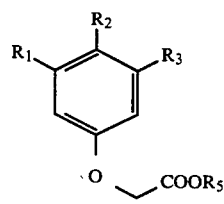

(IX)

wherein $R_1$ to $R_3$ and $R_5$ are as defined hereinbefore, with a compound of formula (X):

(X)

wherein $R_5$ is as defined hereinbefore.

The reaction between the compounds of formulae (IX) and (X) is, preferably, carried out in the presence of a base, in particular a metal alkoxide, such as sodium ethoxide.

The compound of formula (IX), wherein $R_2$ is hydrogen, fluoro, chloro or bromo, may be prepared by esterifying a compound of formula (XI):

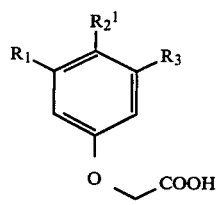

(XI)

wherein $R_2{}^1$ is hydrogen, fluoro, chloro or bromo and $R_1$ and $R_3$ are as defined hereinbefore.

The esterification of a compound of formula (XI) may be carried out conventionally with, for example, a $C_{1-4}$ alkanol, such as ethanol, in the presence of a base, such as sodium hydroxide.

The compound of formula (IX), wherein $R_2$ is hydrogen or $C_{1-4}$ alkyl, may be prepared by reacting a compound of formula (XII):

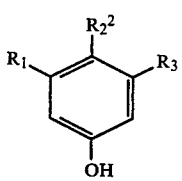

(XII)

wherein $R_2^2$ is hydrogen or $C_{1-4}$ alkyl and $R_1$ and $R_3$ are as defined hereinbefore, with a compound of formula (XIII):

$$BrCH_2COOR_5 \quad (XIII)$$

wherein $R_5$ is as defined hereinbefore.

The reaction between the compounds of formulae (XII) and (XIII) may be carried out conventionally, for example, in the presence of a base, such as potassium carbonate.

The compounds of formulae (X), (XI), (XII) and (XIII) are known or their preparation can be accomplished in an analogous manner to the preparation of such known compounds.

The compound of formula (V), wherein $X^1$ is sulphur, sulphoxide or sulphone, may be prepared by reacting magnesium and methyl iodide with a compound of formula (XIV):

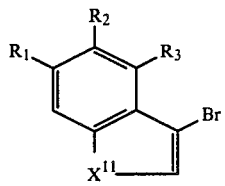

(XIV)

wherein $X^{11}$ is sulphur, sulphoxide or sulphone and $R_1$ to $R_3$ are as defined hereinbefore, reacting the Grignard reagent so formed with carbon dioxide, and then decomposing the resulting complex with mineral acid; and optionally converting $R_2$ or $R_4$ in the resulting compound of formula (V) into another $R_2$ or $R_4$ respectively.

The reaction of a compound of formula (XIV) with magnesium and methyl iodide, the reaction of the Grignard reagent so formed with carbon dioxide, and the decomposition of the resulting complex, may all be carried out conventionally.

In the reaction of a compound of formula (XIV) with magnesium and methyl iodide, it is preferred that $R_2$ is not bromo since otherwise a competing side-reaction may occur. If it is desired to prepare the compound of formula (V), wherein $R_2$ is bromo, then it is preferred to use the corresponding compound of formula (XIV), wherein $R_2$ is hydrogen, in the reaction with magnesium and methyl iodide and afterwards to convert the hydrogen atom in the resulting compound of formula (V) into bromo, the conversion being carried out as described hereinbefore in relation to compounds of formula (II). In fact, it is even more preferred not to convert the hydrogen atom into bromo until after the reduction of the compound of formula (V) has been carried out, as described hereinbefore. It is possible that a side-reaction may also occur in the reaction of a compound of formula (XIV), wherein $R_2$ is chloro, and magnesium and methyl iodide but any side-reaction that does occur can be mimimised by the use of appropriate conditions well known in the art.

It is particularly preferred that $R_4$, which is hydrogen in the resulting compound of formula (V), is converted to methyl by, for example, transesterification using thionyl chloride, and methanol and triethylamine. The subsequent reduction of the compound of formula (V) may then be carried out in the preferred manner.

The compound of formula (XIV) may be prepared by bromination of a compound of formula (XV):

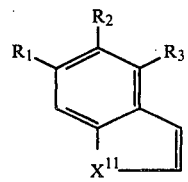

(XV)

wherein $X^{11}$ and $R_1$ to $R_3$ are as defined hereinbefore.

The bromination may be carried out by using bromine in a solvent, such as chloroform, and adding it to a solution of a compound of formula (XV).

The compounds of formula (XV) are known or their preparation can be accomplished in an analogous manner to the preparation of such known compounds.

Alternatively, the compound of formula (V), wherein $X^1$ is sulphur, sulphoxide or sulphone and $R_2$ is hydrogen, fluoro, chloro or bromo, may be prepared by oxidising an aldehyde of formula (XVI):

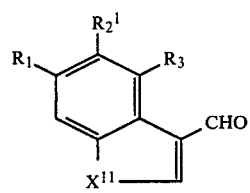

(XVI)

wherein $R_1$, $R_2^1$, $R_3$ and $X^{11}$ are as defined hereinbefore; and optionally converting $R_2^1$ or $R_4$ in the resulting compound of formula (V) into another $R_2^1$ or $R_4$ respectively.

The oxidation of the aldehyde of formula (XVI) may be carried out by treatment with one equivalent of N-bromosuccinimide followed by alkaline hydrolysis using, for example, 10% sodium carbonate solution.

Examples of an optional conversion of $R_2^1$ in the resulting compound of formula (V) into another $R_2^1$ include those mentioned hereinbefore in relation to $R_2$ in the preparation of a compound of formula (I).

It is particularly preferred that $R_4$, which is hydrogen in the resulting compound of formula (V), is converted to methyl by, for example, transesterification in the manner described hereinbefore.

The compound of formula (XVI) may be prepared by oxidising a compound of formula (XVII):

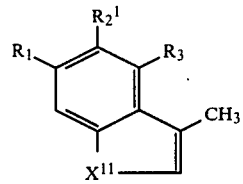

(XVII)

wherein $R_1$, $R_2^1$, $R_3$ and $X^{11}$ are as defined hereinbefore.

The oxidation of the compound of formula (XVII) may be carried out by treatment with two equivalents of N-bromosuccinimide followed by alkaline hydrolysis using, for example, 10% sodium carbonate solution.

It is particularly preferred that the compound of formula (V), wherein $R_2$ is hydrogen, fluoro, chloro or bromo, is prepared in one operation from a compound of formula (XVII) with the compound of formula (XVI) being formed in situ.

The compound of formula (XVII) may be prepared by cyclising a compound of formula (XVIII):

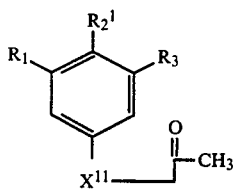
(XVIII)

wherein $R_1$, $R_2^1$, $R_3$ and $X^{11}$ are as defined hereinbefore.

The cyclisation of a compound of formula (XVIII) may be achieved under anhydrous conditions using phosphorus pentoxide at an elevated temperature, or, preferably, using polyphosphoric acid at moderate temperature.

The compound of formula (XVIII) may be prepared by reacting a compound of formula (XIX):

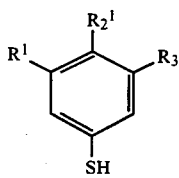
(XIX)

wherein $R_1$, $R_2^1$ and $R_3$ are as defined hereinbefore, with acetylmethyl chloride in the presence of base, such as sodium hydroxide.

The compounds of formula (XIX) are known or their preparation can be accomplished in an analogous manner to the preparation of such known compounds.

As a further alternative, the compound of formula (II), wherein $X^1$ is oxygen and $R_1$ to $R_4$ are as defined hereinbefore, may be prepared by reacting a compound of formula (XX):

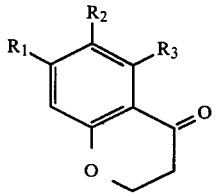
(XX)

wherein $R_1$ to $R_3$ are as hereinbefore defined, with thallium trinitrate and a $C_{1-4}$ alkanol on K-10 clay; and optionally converting $R_4$ in the resulting compound of formula II into another $R_4$.

The mixture of thallium trinitrate and a $C_{1-4}$ alkanol on K-10 clay is a ring contracting reagent which is described by E. C. Taylor, et. al., in J. Am. Chem. Soc., 1976, 98, 6750 et seq. It is prepared from thallium trinitrate, tri $C_{1-4}$ alkyl orthoformate and K-10 clay, and it results in a compound of formula (II), wherein $R_4$ is an alkyl group corresponding to the $C_{1-4}$ alkanol employed in the reagent.

The $C_{1-4}$ alkyl group for $R_4$ in the resulting compound of formula (II) may be optionally converted into hydrogen using 10% aqueous sodium hydroxide solution. The hydrogen atom for $R_4$ may then be optionally converted into a different $C_{1-4}$ alkyl group using 2% $C_{1-4}$ alcoholic hydrogen chloride solution. Both these conversions are required, and may, preferably, be carried out in one operation by transesterification, when it is desired to obtain a $C_{1-4}$ alkyl group for $R_4$ which is different from that obtained directly from the ring contracting reaction.

The compounds of formula (XX) are known or their preparation can be accomplished in an analogous manner to the preparation of such known compounds.

The compound of formula (IV) may be prepared by hydrolysis of a compound of formula (XXI):

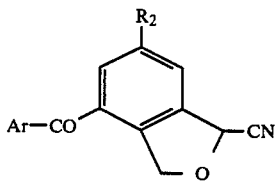
(XXI)

wherein Ar and $R_2$ are as hereinbefore defined.

The hydrolysis of a compound of formula (XXI) may be carried out using an aqueous mineral acid.

It is greatly preferred that the second sub-group of compounds of formula (I), are prepared in one operation from a compound of formula (XXI) with the compound of formula (IV) being formed in situ.

The compound of formula (XXI) may be prepared by cyclising a compound of formula (XXII):

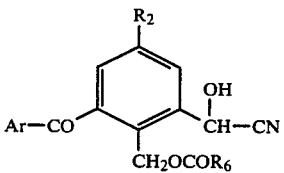
(XXII)

wherein Ar and $R_2$ are as hereinbefore defined, and $R_6$ is $C_{1-4}$ alkyl, such as methyl.

The compound of formula (XXII) may be prepared by reacting a compound of formula (XXIII):

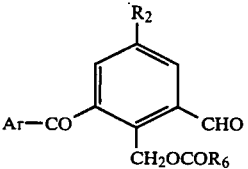
(XXIII)

wherein Ar, $R_2$ and $R_6$ are as hereinbefore defined, either with an alkali metal cyanide and a dilute mineral acid or with trimethylsilyl cyanide followed by a mineral acid.

The reaction of a compound of formula (XXIII) with an alkali metal cyanide and a dilute mineral acid gives the desired compound of formula (XXII) directly. However, improved yields are obtained with the alternative route, which proceeds through a trimethylsilyl ether intermediate, and accordingly this route is preferred.

Preferably, the alkali metal cyanide is sodium cyanide and the dilute mineral acid is dilute sulphuric acid.

Preferably, the reaction with trimethylsilyl cyanide is carried out under an inert atmosphere.

Preferably, the mineral acid employed in the reaction with the trimethylsilyl ether intermediate is hydrochloric acid, and preferably the reaction is also carried out under an inert atmosphere.

The compound of formula (XXIII) may be prepared by reacting a compound of formula (XXIV):

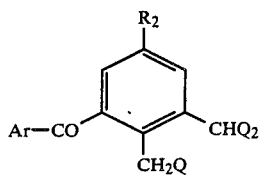

(XXIV)

wherein Ar and $R_2$ are as hereinbefore defined, and Q is bromo, chloro or $C_{1-4}$ alkanoyloxy, with an alkali metal alkanoate.

Preferably, Q is bromo.

The reaction may conveniently be carried out in an aqueous $C_{1-4}$ alkanoic acid solvent, the acid corresponding to the alkanoate.

Preferably, the solvent is glacial acetic acid and the alkanoate is acetate, in particular sodium acetate.

A compound of formula (XXIV) may be prepared by reacting a compound of formula (XXV):

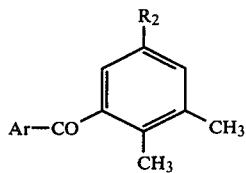

(XXV)

wherein Ar and $R_2$ are as hereinbefore defined, with three equivalents of N-bromosuccinimide, in the case of Q being bromo, sulphuryl chloride, in the case of Q being chloro, and lead tetraalkanoate, in the case of Q being $C_{1-4}$ alkanoyloxy.

The reaction leads to the di-Q-substituted intermediate and then the intermediate reacts with a further equivalent to give the desired tri-Q-substituted product of formula (XXIV).

Preferably, Q is bromo and the reaction is carried out under free radical conditions, the radical initiator being dibenzoyl peroxide and light. When Q is chloro, the reaction may optionally employ a radical initiator. When Q is $C_{1-4}$ alkanoyloxy, the reaction is preferably carried out in the corresponding alkanoic acid optionally containing the corresponding alkanoyl anhydride.

A compound of formula (XXV) may be prepared by reacting a compound of formula (XXVI):

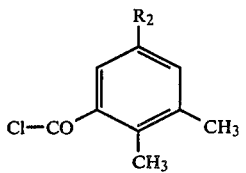

(XXVI)

wherein $R_2$ is as hereinbefore defined, with a compound of formula (XXVII):

Ar—H    (XXVII)

wherein Ar is as hereinbefore defined.

The reaction is carried out under conventional Friedel-Craft conditions, such as in dichloroethane, in the presence of a Lewis acid, such as aluminium trichloride.

A compound of formula (XXVI) may be prepared by reacting a compound of formula (XXVIII):

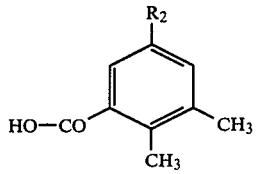

(XXVIII)

wherein $R_2$ is as hereinbefore defined, with thionyl chloride.

The reaction may be carried out in benzene and conveniently the Friedel-Craft solvent and Lewis acid may be added to the reaction mixture without isolation of the compound of formula (XXVI).

The compounds of formula (XXVII) and (XXVIII) are known or their preparation can be accomplished in a manner analogous to the preparation of such known compounds.

The present invention further provides a pharmaceutical composition, which comprises a compound of formula (I), or a pharmaceutically acceptable salt thereof, and a pharmaceutically acceptable carrier.

A composition of this invention is useful in the treatment of pain and/or in the treatment of rheumatism and arthritis or other analgesic and inflammatory conditions.

A composition of the invention, which may be prepared by admixture, may contain a diluent, binder, filler, disintegrant, flavouring agent, colouring agent, lubricant, preservative or the like in conventional manner. These conventional excipients may be employed in conventional manner, for example as in the preparation of compositions of ketoprofen, indomethacin, naproxen, acetylsalicylic acid and other analgesic or anti-inflammatory agents.

A composition of the invention may be adapted for oral, rectal, topical or parenteral, intravenous or intramuscular administration but oral administration is preferred.

A composition of the invention will preferably be in the form of a unit dose, such as a tablet or capsule or a sachet containing reconstitutable powder. A unit dose will generally contain from 20 to 1000 mg and preferably will contain from 30 to 500 mg in particular 50, 100, 150, 200, 250, 300, 350, 400, 450 or 500 mg. The composition may be administered once or more times a day, for example, 2, 3 or 4 times daily, so that the total daily dose for a 70 kg adult will normally be in the range 100 to 3000 mg. Alternatively the unit dose will contain from 2 to 20 mg of a compound of the invention and be administered in multiples, if desired, to give the preceeding daily dose.

A particular composition of the invention is a hard gelatin capsule containing the required amount of a compound of the invention in the form of a powder or granulate in intimate mixture with a lubricant, such as magnesium stearate, a filler, such as microcrystalline cellulose, and a disintegrant, such as sodium starch glycollate.

The present invention additionally provides a method of treating a painful and/or inflammatory condition in a mammal, such as a human being, which comprises administering an analgesic or anti-inflammatory effective amount of a compound, pharmaceutically acceptable salt, or composition of the invention to the mammal.

The present invention further provides a compound, pharmaceutically acceptable salt, or composition of the invention for use in the treatment of a painful and/or inflammatory condition.

The following Descriptions and Examples illustrate the preparation of compounds of the invention and the following biological data illustrates their pharmacological, in particular, analgesic and/or anti-inflammatory activity.

DESCRIPTION 1

Preparation of 5-bromo-2,3-dihydrobenzofuran-3-carboxylic acid (D1)

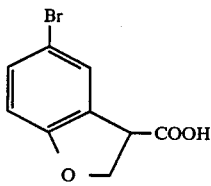
(D1)

A solution of 6-bromo-4-chromanone (36.5 g, 0.16 mole) in dry dichloromethane (200 ml) was added to a stirred suspension of thallium trinitrate (0.24 mole) absorbed onto K10 clay (240 g)[1] in dry dichloromethane (800 ml). The mixture was stirred at room temperature for 2½ hours and the solid then removed by filtration through kieselguhr. The filtrate was washed with water (2×400 ml) and brine (1×400 ml), then dried ($Na_2SO_4$) and evaporated to dryness to give a yellow solid (38 g). This material was dissolved in methanol (200 ml), a solution of sodium hydroxide (19.2 g, 0.48 mole) in water (300 ml) added and the mixture stirred at room temperature overnight. The solution was then concentrated to about half its volume and the residual mixture acidified with 5N hydrochloric acid. This acidic mixture was extracted with ethyl acetate (2×200 ml) and the organic solution then extracted with aqueous sodium hydrogen carbonate solution (2×200 ml). The basic solution was acidified with 5N hydrochloric acid and then extracted with ethyl acetate (2×200 ml). The organic solution was washed with water (2×100 ml) and brine (1×100 ml), dried ($Na_2SO_4$) and evaporated to dryness to give the title compound as a yellow solid (7.0 g, 18%).

NMR: ($CDCl_3$) 4.1-5.0 (m,3H), 6.59 (d,J=8 Hz, 1H), 7.19 (dd, J=8 Hz and 2 Hz, 1H), 7.42 (d,J=2 Hz,1H), 11.03(br.s, 1H).

[1]E. C. Taylor et.al., *J.Amer.Chem.Soc.*, 1976, 98, 6750 et seq.

DESCRIPTION 2

Preparation of ethyl 5-bromo-2,3-dihydrobenzofuran-3-carboxylate (D2)

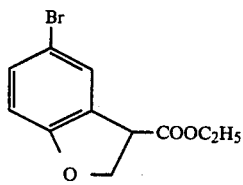
(D2)

The acid (7.0 g, 0.029 mole, D1) was dissolved in 2% ethanolic HCl (200 ml) and the solution heated under reflux for 2 hours. It was then diluted with water (500 ml) and concentrated to about half its volume. The residue was extracted with ether (2×200 ml) and the organic solution washed with water (2×100 ml) and brine (1×100 ml) dried ($Na_2SO_4$) and evaporated to dryness to leave an orange oil. This was purified by column chromatography on silica gel, eluting with 10% ether/pentane, to give the title compound as a yellow oil (5.69 g, 73%).

NMR: δ ($CDCl_3$) 1.28(t,J=7 Hz,3H), 4.16 (q,J=7 Hz,2H), 4.1-5.0(m,3H), 6.57(d,J=8 Hz,1H), 7.17(dd, J=8 Hz and 2 Hz,1H), 7.37 (d,J=2 Hz, 1H).
IR: (film)(cm$^{-1}$)1740.

DESCRIPTION 3

Preparation of 5-chloro-2,3-dihydrobenzofuran-3-carboxylic acid (D3)

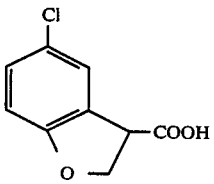
(D3)

The title compound was prepared from 6-chloro-4-chromanone (9.0 g, 0.049 mole) and thallium trinitrate (0.074 mole) absorbed onto K10 clay (75 g) by the method of Description 1, as a yellow solid (1.51 g, 16%).

NMR: δ ($CDCl_3$) 4.1-5.0 (m,3H) 6.63 (d,J=8 Hz,1H), 7.07 (dd,J=8 Hz and 2 Hz, 1H), 7.27 (d,J;32 2 Hz,1H), 10.67 (br.s., 1H).

DESCRIPTION 4

Preparation of ethyl 5-chloro-2,3-dihydrobenzofuran-3-carboxylate (D4)

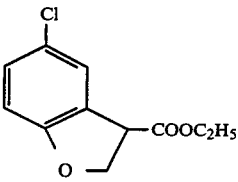
(D4)

The title compound was prepared from the dihydrobenzofuran acid (1.51 g, 0.0076 mole, (D3)) by the method give in Description 2, as a yellow oil (1.44 g, 84%).

NMR: δ ($CDCl_3$) 1.30 (t,J=7 Hz,3H), 4.20 (q,J=7 Hz,2H), 4.1-5.0(m,3H), 6.68(d,J=8 Hz,1H) 7.17 (dd, J=8 Hz and 2 Hz,1H), 7.30(d,J=2 Hz,1H).
IR:(film)(cm$^{-1}$) 1740.

DESCRIPTION 5

Preparation of 2,3-dimethylbenzoyl chloride (D5)

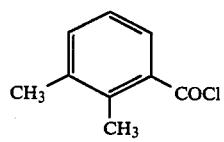
(D5)

2,3-dimethylbenzoic acid (35.0 g, 233 mmol) was heated to reflux temperature, in dry benzene (80 ml)

containing thionyl chloride (45.0 g, 378 mmol) for five hours. The mixture was cooled, filtered and evaporated under reduced pressure to give 2,3-dimethylbenzoyl chloride (36.0 g, 92%) as an oil.

NMR: δ (CDCl₃) 2.26 (s,3H), 2.36 (s,3H), 6.90–7.96 (m,3H).

IR: (film)(cm⁻¹) 1766.

DESCRIPTION 6

Preparation of 1-benzoyl-2,3-dimethylbenzene (D6)

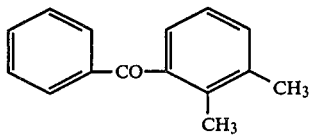

(D6)

To a stirred solution of 2,3-dimethylbenzoyl chloride (35 g, 208 mmol) at 0° in dry dichloroethane (80 ml) was added anhydrous aluminium chloride (27.7 g, 208 mmol) portionwise over two minutes. The mixture was stirred for fifteen minutes and dry benzene (40 ml) was added. After warming to room temperature over fifteen minutes, the mixture was heated to reflux for four hours. The dark solution was cooled, poured onto ice (200 ml) containing concentrated hydrochloric acid (20 ml) and extracted with ether (3×100 ml). The combined organic layers were washed with 10% sodium hydroxide (2×50 ml), 10% sodium carbonate (50 ml) and brine (50 ml). After drying the organic layer over sodium sulphate, the solvent was removed under reduced pressure and the red oil (36 g) so obtained was chromatographed (SiO₂(400 g) using petroleum ether (60°–80°) and chloroform (0–12%) as eluent). This gave the desired 1-benzoyl-2,3-dimethylbenzene (18.2 g, 42%).

NMR: δ (CCl₄) 2.1(s,3H), 2.23(s,3H), 6.75–7.75 (m,8H).

IR: (film) (cm⁻¹) 1665.

DESCRIPTION 7

Preparation of 1-benzoyl-2,3-bis(bromomethyl)benzene (D7)

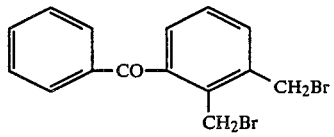

(D7)

1-Benzoyl-2,3-dimethylbenzene (8.62 g, 41 mmol) was dissolved in carbon tetrachloride (100 ml) and recrystallized N-bromosuccinimide (14.8 g, 83 mmol) and dibenzoyl peroxide (50 mg) were added. The mixture was heated to reflux for two hours, cooled and filtered. The solid was washed with carbon tetrachloride (50 ml) and the combined organic layers were evaporated under reduced pressure to give crude 1-benzoyl-2,3-bis(bromomethyl)benzene (15.1 g, ca. 100% recovery).

NMR: δ (CCl₄/CDCl₃) 4.53 (s,2H), 4.62 (s,2H), 6.95–7.75 (m,8H).

DESCRIPTION 8

Preparation of 1-benzoyl-2-bromomethyl-3-(dibromomethyl)benzene (D8)

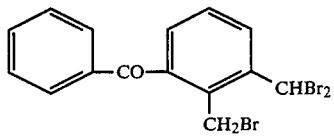

(D8)

1-Benzoyl-2,3-bis(bromomethyl)benzene (8.0 g, 22 mmol) (crude, Description 7) was dissolved in carbon tetrachloride (50 ml) and recrystallized N-bromosuccinimide (3.9 g 22 mmol) and dibenzoyl peroxide (100 mg) were added. The mixture was heated to reflux for sixteen hours, cooled and filtered. The solid was washed with carbon tetrachloride (2×10 ml) and the combined organic layers were evaporated under reduced pressure to give crude 1-benzoyl-2-bromomethyl-3-(dibromomethyl)benzene (9.0 g, 93% recovery).

NMR: δ (CDCl₃) 4.47 (2H,s), 6.92 (1H,s).

DESCRIPTION 9

Preparation of 2-acetoxymethyl-3-benzoyl benzaldehyde (D9)

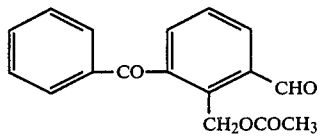

(D9)

To a stirred solution of crude 1-benzoyl-2-bromomethyl-3-(dibromomethyl)benzene (2.3 g, 5 mmol) in glacial acetic acid (30 ml) was added sodium acetate (4.5 g, 55 mmol) in water (8 ml). The stirred mixture was heated to reflux temperature for sixteen hours, cooled and partitioned between diethylether (100 ml), ethyl acetate (20 ml) and 10% sodium carbonate solution (100 ml). Further solid sodium carbonate was added until effervescence ceased. The organic layer was washed with 10% sodium carbonate solution (30 ml) and brine (30 ml) and dried over sodium sulphate. Removal of the solvent under reduced pressure gave an oil (1.1 g) that was chromatographed (SiO₂(40 g) using (4:1) pentane:ethyl acetate as eluent). This gave 2-acetoxymethyl-3-benzoylbenzaldehyde (0.35 g, 22% from 1-benzoyl-2,3-dimethylbenzene).

NMR: δ (CDCl₃) 1.70 (s,3H), 5.43 (s,2H), 7.1–8.2 (m,8H), 10.23 (s,1H).

DESCRIPTION 10

Preparation of 2([2-acetoxymethyl-3-benzoyl]phenyl)-2-trimethylsiloxyacetonitrile (D10)

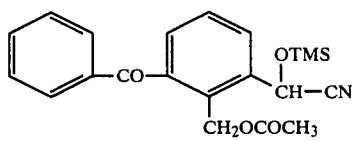

(D10)

2-Acetoxymethyl-3-benzoylbenzaldehyde (0.29 g, 1 mmol) was treated with trimethylsilylcyanide (0.10 g, 1 mmol) under nitrogen. The mixture was heated on an oil bath (bath temperature 65°) for two hours. A further portion of trimethylsilylcyanide (0.10 g, 1 mmol) was added followed by a small crystal of anhydrous zinc iodide. After heating for a further half an hour (bath temperature 65°) the mixture was stirred at room temperature for sixteen hours. N.M.R. analysis then found this oil to be 2([2-acetoxymethyl-3-benzoyl]phenyl)-2-trimethylsiloxyacetonitrile.

N.M.R.: δ (CDCl$_3$)0.25 (s,9H), 1.74 (s,3H), 5.12 (s,2H), 5.76 (s,1H), 7.1–7.8 (8H,m).

DESCRIPTION 11

(A) Preparation of 6-bromo-4-chromanone (D11)

(D11)

The title compound was prepared by the method of Canalini et al.[2] by the reaction of 4-bromophenol (40 g, 0.23 mole) and methyl acrylate (100 ml) in the presence of Triton B (6 ml of a 40% solution in methanol); followed by dilute acid hydrolysis of the resulting ester and cyclisation of the (4-bromophenoxy)propionic acid in concentrated sulphuric acid. The product was recrystallised from petroleum ether (60°–80° C.) to give a white crystalline solid (6.80 g, 13%). M.p. 78°–80° C.

NMR: δ (CDCl$_3$) 2.72 (t, J=6 Hz, 2H), 4.43 (t, J=6 Hz, 2H), 6.72 (d, J=9 Hz, 1H), 7.39 (dd, J=9 Hz and 2 Hz, 1H), 7.85 (d, J=2 Hz, 1H).

[2]G. Canilini et. al., Ann.Chim., 1967, 57, 1045-72. (C.A. 1967, 69, 2798q).

(B) Preferred method for the preparation of 6-bromo-4-chromanone (D11)

4-Bromophenol (105 g, 0.61 mole) was converted into methyl(4-bromophenoxy)propanoate by the method referred to in Description 11A. This ester (125 g, 0.48 mole) was then added slowly to concentrated sulphuric acid (500 ml) and the resulting yellow solution stirred at room temperature for 30 minutes. This solution was poured slowly into ice/water (5 liters) and the mixture extracted using ethyl acetate (2×700 ml). The organic solution was washed with 10% sodium carbonate solution (2×300 ml) and brine (1×300 ml), dried (Na$_2$SO$_4$) and evaporated to dryness to give a pale yellow solid. This was recrystallised from ethyl acetate/petroleum ether (60°–80° C.) to give the title compound as a white crystalline solid (43.4 g, 31%). M.p. 79°–80°.

DESCRIPTION 12

Preparation of 6-fluoro-4-chromanone (D12)

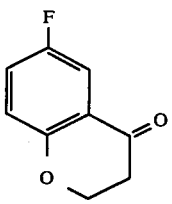
(D12)

The title compound was prepared from 4-fluorophenol (77 g, 0.69 mole) by a method analogous to that given in Description 11B, as a white crystalline solid (39.9 g, 35%). M.p. 115°.

NMR: δ (CDCl$_3$) 2.73 (t, J=6 Hz, 2H), 4.43 (t, J=6 Hz, 2H), 6.7–7.6 (m, 3H).

MS: Calculated mass for C$_9$H$_7$FO$_2$=166.0430.

| Analysis | | Calculated | Found |
|---|---|---|---|
| C$_9$H$_7$FO$_2$ | C | 65.05 | 65.25 |
| | H | 4.20 | 4.40 |

DESCRIPTION 13

Preparation of 5-fluoro-2,3-dihydrobenzofuran-3-carboxylic acid (D13)

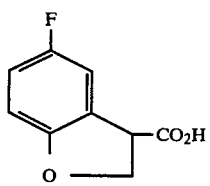
(D13)

The title compound was prepared from 6-fluoro-4-chromanone (D12) (9.96 g, 0.06 mole) and thallium trinitrate (0.083 mole) on K10 clay (84 g) by the method of Description 1, as a yellow solid, (1.66 g, 15%).

NMR: δ (CDCl$_3$) 4.0–5.0 (m, 3H), 6.5–7.3 (m, 3H), 10.0 (br.s, 1H).

DESCRIPTION 14

Preparation of ethyl 5-fluoro-2,3-dihydrobenzofuran-3-carboxylate (D14)

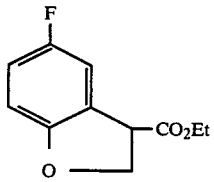
(D14)

The title compound was prepared from the dihydrobenzofuran acid (1.66 g, 0.0091 mole, (D13)) by the method given in Description 2, as a yellow solid (1.82 g, 95%).

NMR: δ (CDCl$_3$) 1.3 (t, J=7 Hz, 3H), 3.9–5.0 (m, 5H), 6.5–7.2 (m, 3H).

DESCRIPTION 15

Preparation of 3-bromobenzothiophene (D15)

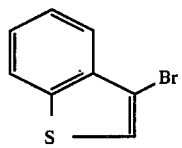
(D15)

A solution of bromine (20.4 ml, 0.40 mole) in chloroform (100 ml) was added dropwise over 1 hour to a stirred mixture of benzothiophene (53.6 g, 0.40 mole) and anhydrous sodium acetate (54.4 g, 0.68 mole) in chloroform (300 ml) at room temperature. The reaction mixture became much thicker during the addition, so a further 300 ml of chloroform was added to aid stirring. After completing the addition, the reaction mixture was stirred for a further 2 hours and then water added (200 ml) to dissolve the inorganic solid. The chloroform layer was separated and washed with water (1×200 ml), sodium hydrogen carbonate solution (1×200 ml) and brine (1×200 ml); then dried (MgSO₄) and evaporated to dryness to give a quantitative yield of the title compound as a yellow oil.

NMR: δ (CDCl₃) 7.1-7.5 (m, 2H), 7.35 (s, 1H) 7.6-7.9 (m, 2H).

DESCRIPTION 16

Preparation of benzothiophene-3-carboxylic acid (D16)

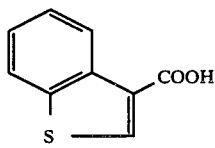
(D16)

A solution of 3-bromobenzothiophene (0.40 mole, (D15)) and methyl iodide (25 ml, 0.40 mole) in dry ether (400 ml) was added to a stirred mixture of magnesium turnings (24 g, 1.0 mole) and dry ether (100 ml) under nitrogen, at such a rate as to maintain a steady reflux. After the addition was complete, the reaction mixture was heated under reflux for 30 minutes and then allowed to cool to room temperature. The solution was diluted with dry toluene (500 ml) and stirred vigorously as dry carbon dioxide was bubbled through over 3 hours. The thick precipitate which formed was dissolved by the addition of dilute hydrochloric acid and the organic layer was then separated. The aqueous solution was extracted with ethyl acetate (2×300 ml) and all the organic solutions were then combined and extracted with 10% sodium carbonate solution (4×300 ml). The aqueous extracts were combined, washed with ether (2×200 ml) and then acidified with dilute hydrochloric acid. The precipitate was filtered off, washed with water and then dried under vacuum to give the title compound as a white solid (31.2 g, 44%) m.p. 171°-173°.

NMR: δ (CDCl₃) 7.2-7.6 (m, 2H), 7.7-8.0 (m, 1H), 8.55 (s, 1H), 8.5-8.8 (m, 1H), 11.0-11.6 (br. s, 1H).

DESCRIPTION 17

Preparation of methyl benzothiophene-3-carboxylate (D17)

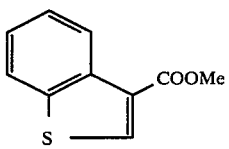
(D17)

A stirred mixture of the acid (27.7 g, 0.156 mole, (D16)) and thionyl chloride (22.7 ml, 0.31 mole) in dry toluene (300 ml) was heated under reflux for 1 hour. The solution was then evaporated to dryness to leave a red oil. This was dissolved in dry ether (300 ml), the solution cooled in an ice bath, and treated with dry triethylamine (43 ml, 0.31 mole) followed by methanol (12.6 ml, 0.31 mole). The mixture was stirred at room temperature for 20 minutes, before acidifying with dilute hydrochloric acid. The organic layer was separated and the aqueous solution extracted with ether (1×150 ml). The organic solutions were combined and washed with 10% sodium carbonate solution, dilute hydrochloric acid and water; then dried (MgSO₄) and evaporated to dryness to give the title compound as a red oil (90%).

NMR: δ (CDCl₃) 3.88 (s, 3H), 7.2-7.6 (m, 2H), 7.7-8.0 (m, 1H), 8.37 (s, 1H), 8.5-8.8 (m, 1H).

DESCRIPTION 18

Preparation of methyl 2,3-dihydrobenzothiophene-3-carboxylate (D18)

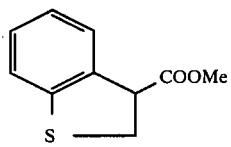
(D18)

A solution of the benzothiophene ester (0.14 mole, (D17)) in methanol (800 ml) was stirred together with magnesium turnings (13.5 g, 0.56 mole) at room temperature. After a short initiation period of about 5 minutes, hydrogen gas was seen to be evolved and the reaction temperature began to rise rapidly. The reaction mixture was kept at about 30° by intermittent cooling in an acetone/cardice bath. After all the magnesium had reacted, the solution was acidified with dilute hydrochloric acid and then diluted with water (5 liters). The mixture was extracted with ether (3×600 ml), the organic solution washed with water (2×400 ml) and brine (1×400 ml), then dried (MgSO₄) and evaporated to dryness to give the title compound as a red oil (90%).

NMR: δ (CDCl₃) 3.2-3.9 (m, 2H), 3.68 (s, 3H), 4.1-4.4 (m, 1H), 6.8-7.3 (m, 4H).

DESCRIPTION 19

(A) Preparation of ethyl 2,3-dihydrobenzothiophene-3-carboxylate (D19)

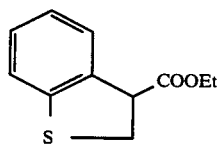
(D19)

Ethanol (300 ml) under nitrogen was treated portionwise with sodium hydride (600 mg of 80% disperson in oil, 0.020 mole) and the solution then stirred for 5 minutes before adding a solution of the methyl ester (15.5 g, 0.080, (D18)) in ethanol (50 ml). The solution was stirred for 1 hour at room temperature, then acidified with dilute hydrochloric acid, diluted with water (1.5 liters) and extracted with ether (2×300 ml). The ether solutions were combined, washed with water, dried (MgSO4) and evaporated to dryness to give the title compound as a yellow oil (15.6 g, 94%).

NMR: δ (CDCl3) 1.27 (t, J=7 Hz, 3H), 3.2-3.9 (m, 2H), 4.1-4.4 (m, 1H), 4.17 (q, J=7 Hz, 2H), 6.8-7.3 (m, 4H).

(B) Alternative preparation of ethyl 2,3-dihydrobenzothiophene-3-carboxylate (D19)

Sodium (9.0 g, 0.39 mole) in small portions was added to a stirred solution of the benzothiophene acid (6.9 g, 0.039 mole, (D16)) in ethanol (150 ml) and under nitrogen over 1 hour, keeping the temperature below 50° C. by intermittent cooling in an ice/water bath. After all the sodium had reacted, the solution was diluted with water (800 ml), acidified with dilute hydrochloric acid and then extracted with ethyl acetate (2×300 ml). The organic solution was washed with water (2×200 ml), dried (MgSO4) and evaporated to dryness to leave a white solid. This was dissolved in 0.5% ethanolic HCl (200 ml) and heated under reflux for 1 hour. The solution was allowed to cool, then diluted with water (1 liter) and extracted with ether (2×300 ml). The organic extracts were combined and washed with 10% sodium carbonate solution (1×200 ml), dilute hydrochloric acid (1×200 ml) and brine (1×200 ml), then dried (MgSO4) and evaporated to dryness to leave a yellow oil. This was chromatographed on a silica gel column eluting with 5% ether/pentane to give the title compound as a colourless oil (1.22 g, 15%).

DESCRIPTION 20

Preparation of ethyl 5-bromo-2,3-dihydrobenzothiophene-3-carboxylate (D20)

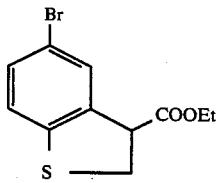
(D20)

A stirred solution of the dihydrobenzothiophene ester (15.7 g, 0.075 mole, (D19)) in glacial acetic acid (200 ml) was treated dropwise at room temperature with a solution of bromine (3.85 ml, 0.075 mole) in glacial acetic acid (25 ml). After the addition was complete, the reaction mixture was stirred for a further 2½ hours before diluting with water (1 liter). The mixture was extracted with ether (2×400 ml), the extracts combined and washed with water, 10% sodium carbonate solution, dilute hydrochloric acid and brine, then dried (MgSO4) and evaporated to dryness to leave a red oil. This was chromatographed on silica gel eluting with 15% ether/pentane to give the title compound as a yellow oil (16.3 g, 75%) b.p. 145°-155° at 0.02 mmHg.

NMR: δ (CDCl3) 1.30 (t, J=7 Hz, 3H), 3.2-3.9 (m, 2H), 4.1-4.4 (m, 1H), 4.19 (q, J=7 Hz, 2H), 6.97 (d, J=8 Hz, 1H), 7.23 (dd, J=8 Hz and 2 Hz, 1H), 7.40 (d, J=2 Hz, 1H).

DESCRIPTION 21

Preparation of (4-chlorophenylthio)propanone (D21)

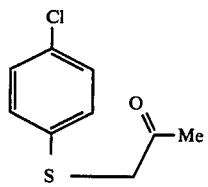
(D21)

A stirred solution of 4-chlorothiophenol (47.1 g, 0.326 mole) in sodium hydroxide solution (14.3 g, 0.358 mole in 750 ml water) was treated dropwise over 20 minutes with freshly distilled chloroacetone (28.5 ml, 0.358 mole) and the resulting mixture was stirred for a further 30 minutes at room temperature. The mixture was extracted with ether (3×200 ml) and the organic solution then washed with 2% sodium hydroxide solution (2×200 ml) and water (2×200 ml), dried (MgSO4) and evaporated to dryness to give a quantitative yield of the title compound as a pale yellow solid. A small sample was recrystallized from pentane to yield a colourless crystalline solid m.p. 37°-38° C.

NMR: δ (CDCl3) 2.25 (s, 3H), 3.63 (s, 2H), 7.27 (s, 4H).

DESCRIPTION 22

Preparation of 5-chloro-3-methylbenzothiophene (D22)

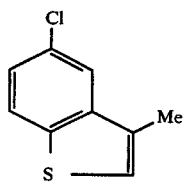
(D22)

The (arylthio) propanone (60 g, 0.3 mole, (D21)) was added portionwise over 20 minutes with stirring to polyphosphoric acid (500 g) at about 90° C. The mixture was stirred at this temperature for a further 15 minutes and then poured into a stirred mixture of ice/water (3 liters). The mixture was extracted with ethyl acetate (2×500 ml) and the organic extract then washed with sodium carbonate solution (2×200 ml), dilute hydrochloric acid (2×200 ml) and brine (2×200 ml); dried (MgSO4) and concentrated to give a red oil. This was purified by distilling under vacuum to give the title compound as a pale yellow oil (39 g, 71%) b.p. 84°-86° C. at 0.02 mmHg.

NMR: δ (CDCl₃) 2.33 (d, J=1 Hz, 3H), 7.00 (d, J=2 Hz, 1H), 7.20 (dd, J=8 Hz and 2 Hz, 1H), 7.55–7.75 (m, 2H).

DESCRIPTION 23

Preparation of 5-chlorobenzothiophene-3-carboxaldehyde (D23)

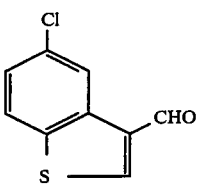
(D23)

A stirred mixture of 5-chloro-3-methylbenzothiophene (39 g, 0.214 mole, (D22)) and recrystallized N-bromosuccinimide (77 g, 0.432 mole) in carbon tetrachloride (700 ml) was illuminated with a 100 W lamp, while heating at reflux temperature for 4 hours. The reaction mixture was allowed to cool, the solid was filtered off and the filtrate was evaporated to dryness to leave a yellow oil. This residue was treated with 10% sodium carbonate solution (450 ml) and heated under rflux, with vigorous stirring, for 5 hours. The mixture was allowed to cool and extracted with chloroform (3×200 ml). The organic solution was washed with brine (2×200 ml), dried (MgSO₄) and evaporated to dryness to give the title compound as a red solid (37 g, 88%).

NMR: δ (CDCl₃) 7.31 (dd, J=9 Hz and 2 Hz, 1H); 7.69 (d, J=9 Hz, 1H); 8.25 (s, 1H); 8.60 (d, J=2 Hz, 1H); 10.08 (s, 1H).

The sodium carbonate portion was acidified with dilute hydrochloric acid and the precipitate formed was filtered off, washed with water and dried under vacuum at 70° C. to give 5-chlorobenzothiophene-3-carboxylic acid (3.7 g, 8%) as a pale yellow solid m.p.>220° C. (dec.)

NMR: δ ((CD₃)₂SO) 7.27 (dd, J=8 Hz and 2 Hz, 1H); 7.80 (d, J=8 Hz, 1H); 8.40–8.50 (m, 2H).

DESCRIPTION 24

Preparation of 5-chlorobenzothiophene-3-carboxylic acid (D24)

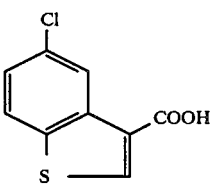
(D24)

A mixture of the aldehyde (37 g, 0.19 mole, (D23) and recrystallised N-bromosuccinimide (35 g, 0.20 mole) in carbon tetrachloride (700 ml) was illuminated with a 100 W lamp, while stirring at reflux temperature for 4 hours. The reaction mixture was allowed to cool, the solid was filtered off and the filtrate was evaporated to dryness to leave a brown solid. This residue was treated with 10% sodium carbonate solution (380 ml) and stirred vigorously at reflux temperature for 3 hours. The mixture was allowed to cool, then filtered to remove the insoluble material and the filtrate was acidified with dilute hydrochloric acid. The precipitate formed was filtered off, washed with water and dried under vacuum at about 70° C. A further sample of this product was obtained by refluxing the insoluble material with more 10% sodium carbonate solution (150 ml) for 1½ hours. The mixture was then allowed to cool and treated as above. The title compound was obtained as a pale yellow solid in combined yield of 22.2 g (55%) m.p.>220° C. (dec.).

DESCRIPTION 25

Preparation of methyl 5-chlorobenzothiophene-3-carboxylate (D25)

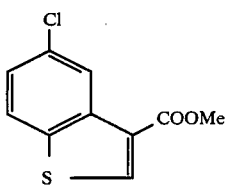
(D25)

The title compound was prepared from the acid (22.2 g, 0.105 mole, (D24)) by the method given in Description 17, as a brown solid (quantitative yield).

NMR: δ (CDCl₃) 3.83 (s, 3H), 7.15 (dd, J=8 Hz and 2 Hz, 1H), 7.55 (d, J=8 Hz, 1H), 8.18 (s, 1H), 8.40 (d, J=2 Hz, 1H).

DESCRIPTION 26

Preparation of methyl 5-chloro-2,3-dihydrobenzothiophene-3-carboxylate (D26)

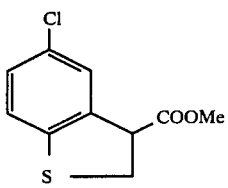
(D26)

The title compound was prepared from the benzothiophene ester (0.105 mole, (D25)) by the method given in Description 18, as a brown oil (21.6 g, 90%).

NMR: δ (CDCl₃) 3.2–3.9 (m, 2H), 3.70 (s, 3H), 4.1–4.4 (m, 1H), 6.9–7.3 (m, 3H).

DESCRIPTION 27

Preparation of ethyl 5-chloro-2,3-dihydrobenzothiophene-3-carboxylate (D27)

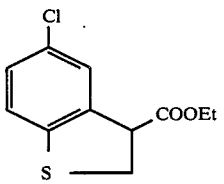
(D27)

The methyl ester (21.6 g, 0.094 mole, (D26)) was transesterified using the method given in Description 19A to yield of a brown oil. This was purified by passage through a silica gel column eluting with 5% ether/pentane to give the title compound as a yellow oil (20.9 g, 92%).

NMR: δ (CDCl₃) 1.30 (t, 7 Hz, 3H), 3.2–3.9 (m, 2H), 4.1–4.4 (m, 1H), 4.19 (q, J=7 Hz, 2H), 7.0–7.3 (m, 3H).

IR: (film) (cm$^{-1}$) 1730.

DESCRIPTION 28

Preparation of ethyl (4-methylphenoxy)acetate (D28)

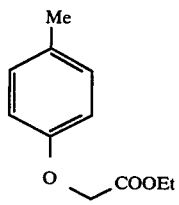
(D28)

A stirred mixture of p-cresol (14.6 g, 0.135 mole) and anhydrous potassium carbonate (37.2 g, 0.27 mole) in dry acetone (200 ml) was heated under reflux for 30 minutes. The mixture was then cooled to room temperature and ethyl bromoacetate (16.6 ml, 0.15 mole) added. The mixture was heated upto reflux again and maintained at this temperature for 4½ hours, then allowed to cool before pouring into water (1000 ml). The aqueous mixture was extracted with ether (2×250 ml) and the organic solution washed with dilute hydrochloric acid (1×200 ml) and water (1×200 ml), then dried (MgSO$_4$) and evaporated to dryness to give a quantitative yield of the title compound as a yellow oil.

NMR: δ (CDCl$_3$) 1.26 (t, J=7 Hz, 3H), 2.23 (s, 3H), 4.17 (q, J=7 Hz, 2H), 4.47 (s, 2H), 6.68 (d, J=8 Hz, 2H), 6.92 (d, J=8 Hz, 2H).

DESCRIPTION 29

Preparation of diethyl 2-(4-methylphenoxy)-3-oxosuccinate (D29)

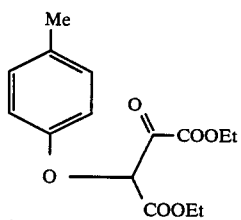
(D29)

A sample of ethanol-free sodium ethoxide was prepared by dissolving sodium (3.0 g, 0.13 mole) in ethanol (50 ml) and then evaporating off the excess solvent. The last traces of ethanol were removed by the addition of dry toluene (50 ml), followed by evaporation to dryness. A stirred suspension of the white solid in dry ether (150 ml) under nitrogen, was treated dropwise with diethyl oxalate (17.6 ml, 0.13 mole) and the yellow solution allowed to stir for 2½ hours at room temperature. A solution of the ethyl phenoxyacetate (0.13 mole, (D28)) in dry ether (50 ml) was added dropwise and the reaction mixture was left to stir overnight, before pouring into water (500 ml). The aqueous layer was separated, washed with ether (1×150 ml) and then acidified with dilute hydrochloric acid. The aqueous mixture was extracted with ether (3×150 ml) and the organic solution then washed with water (2×150 ml), dried (MgSO$_4$) and evaporated to dryness to give the title compound as a yellow oil (28 g, 73%).

NMR: δ (CDCl$_3$) 0.9-1.5 (m, 6H), 2.24 (s, 3H), 3.9-4.5 (m, 4H), 5.65 (s, ketone CH), 6.5-7.2 (m, 4H), 11.1 (s, enol OH).

Integration shows approximately equal mixture of ketone and enol forms.

DESCRIPTION 30

Preparation of diethyl 5-methylbenzofuran-2,3-dicarboxylate (D30)

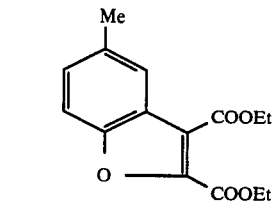
(D30)

The keto diester (28 g, 0.095 mole, (D29)) was slowly added, with stirring, to concentrated sulphuric acid (250 ml) and the resulting orange solution was stirred at room temperature for 15 minutes. This solution was then carefully poured into ice/water (2½ liters) and the mixture extracted with ether (3×300 ml). The organic solution was washed with 10% sodium carbonate solution (2×300 ml), dilute hydrochloric acid (1×300 ml) and water (1×300 ml), then dried (MgSO$_4$) and evaporated to dryness to give the title compound as a yellow oil (10.74 g, 41%).

NMR: δ (CDCl$_3$) 1.40 (t, J=7 Hz, 6H), 2.40 (s, 3H), 4.37 (q, J=7 Hz, 4H), 7.12 (dd, J=8 Hz and 2 Hz, 1H), 7.33 (d, J=8 Hz, 1H), 7.53 (d, J=2 Hz, 1H).

DESCRIPTION 31

Preparation of 5-methylbenzofuran-2,3-dicarboxylic acid (D31)

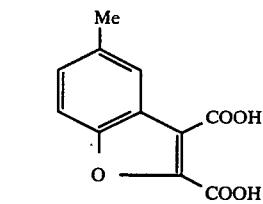
(D31)

A solution of the diester (10.7 g, 0.039 mole, (D30)) in ethanol (50 ml) was treated with 10% sodium hydroxide solution (100 ml) and water (50 ml) and the mixture heated under reflux for 1½ hours. The solution was allowed to cool, concentrated to about half its volume, washed with ether (2×100 ml) and then acidified with dilute hydrochloric acid. The solid was filtered off, washed with water and dried under vacuum at 65° C. to give the title compound as a white solid (6.63 g, 77%). M.p. 270°-280° C. (with decomposition).

DESCRIPTION 32

Preparation of 5-methylbenzofuran-3-carboxylic acid (D32)

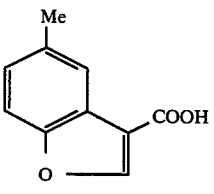
(D32)

The diacid (6.2 g, 0.028 mole, (D31)) was heated under nitrogen upto its melting point around 280° C. and kept at this temperature for 10 minutes. The mixture was allowed to cool to room temperature and the acetone soluble material extracted out. The organic solution was evaported to dryness to leave a yellow solid (3.15 g) containing the title compound as the major component.

NMR: δ (CDCl₃/CD₃COCD₃) 2.42 (s, 3H), 4.8 (br.s), 7.03 (dd, J=8 Hz and 2 Hz, 1H), 7.30 (d, J=8 Hz, 1H), 7.75 (dd, J=2 Hz, 1H), 8.13 (s, 1H).

DESCRIPTION 33

Preparation of methyl 5-methylbenzofuran-3-carboxylate (D33)

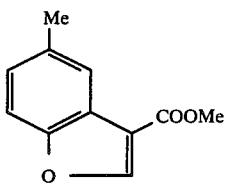

(D33)

The crude benzofuran acid mixture (3.15 g, assume 0.017 mole, (D32)) was esterified by the method given in Description 17 to give a red oil. This was purified by column chromatography on silica gel eluting with 10% ether/pentane, and the resulting pale yellow oil was crystallised from pentane to give the title compound as a white solid (1.40 g, 25% from diacid (D31)) m.p. 40°–41° C.

NMR: δ (CDCl₃) 2.39 (s, 3H), 3.80 (s, 3H), 7.02 (dd, J=8 Hz and 2 Hz, 1H), 7.22 (d, J=8 Hz, 1H), 7.65 (d, J=2 Hz, 1H), 8.02 (s, 1H).

DESCRIPTION 34

Preparation of methyl 5-methyl-2,3-dihydrobenzofuran-3-carboxylate (D34)

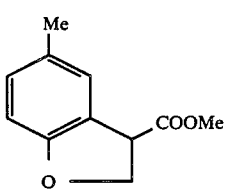

(D34)

The benzofuran ester (1.40 g, 0.0074 mole, (D33)) was reduced by the method given in Description 18 using five equivalents of magnesium, to give the title compound as a pale red oil (1.30 g, 92%).

NMR: δ (CDCl₃) 2.22 (s, 3H), 3.67 (s, 3H), 4.0–5.0 (m, 3H), 6.52 (d, J=8 Hz, 1H), 6.82 (dd, J32 8 Hz and 2 Hz, 1H), 6.97 (d, J=2 Hz, 1H).

DESCRIPTION 35

Preparation of ethyl (4-chlorophenoxy) acetate (D35)

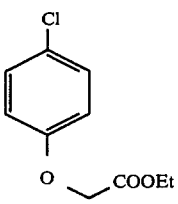

(D35)

A solution of (4-chlorophenoxy) acetic acid (21.1 g, 0.113 mole) in ethanol (250 ml) containing five drops of concentrated hydrochloric acid, was heated under reflux for 2½ h. The solution was allowed to cool, concentrated to about a third of its volume, and then diluted with water (500 ml). The mixture was extracted with ether (2×250 ml) and the organic solution washed with 10% sodium carbonate solution (2×150 ml), dilute hydrochloric acid (2×150 ml) and brine (2×150 ml); then dried and evaporated to dryness to leave a pale yellow oil. This crystallised on standing to give the title compound as a beige solid (21.5 g, 90%).

NMR: δ (CDCl₃) 1.27 (t, J=7 Hz, 3H), 4.21 (q, J=7 Hz, 2H), 4.53 (s, 2H), 6.82 (d, J=9 Hz, 2H), 7.26 (d, J=9 Hz, 2H).

DESCRIPTION 36

Preparation of diethyl 2-(4-chlorophenoxy)-3-oxosuccinate (D36)

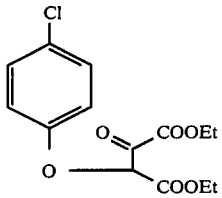

(D36)

The ethyl phenoxyacetate (21.8 g, 0.10 mole, (D35)) was condensed with diethyl oxalate using the method given in Description 29, to give the title compound as a pale yellow oil (31 g, 90%).

NMR: δ (CDCl₃) 1.0–1.5 (m, 6H), 3.9–4.5 (m, 4H), 5.67 (s, ketone CH), 6.6–6.9 (m, 2H), 6.9–7.2 (m, 2H).

Integration shows a mixture of ketone and enol forms.

DESCRIPTION 37

Preparation of diethyl 5-chlorobenzofuran-2,3-dicarboxylate (D37)

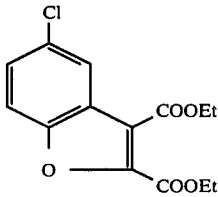

(D37)

The keto diester (7.76 g, 0.025 mole, (D36)) was cyclised by the method given in Description 30 to give a yellow oil. This was purified by column chromatography on silica gel eluting with 20% ether/pentane, and the resulting colourless oil was crystallised from ether/pentane to give the title compound as a white solid (2.8 g, 38%) m.p. 33°–35° C.

NMR: δ (CDCl₃) 1.40 (t, J=7 Hz, 6H), 4.37 (q, J=7 Hz, 4H), 7.30–7.40 (m, 2H), 7.75–7.85 (m, 1H).

| Analysis | | Calculated | Found |
|---|---|---|---|
| C₁₄H₁₃ClO₅ | C | 56.65% | 56.65% |
| | H | 4.40% | 4.35% |
| | Cl | 11.95% | 12.15% |

DESCRIPTION 38

Preparation of 5-chlorobenzofuran-2,3-dicarboxylic acid (D38)

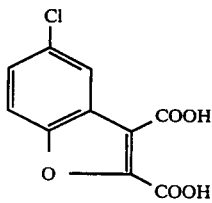

(D38)

The diester (2.4 g, 0.0081 mole, (D37)) was hydrolysed by the method given in Description 31, to give a quantitative yield of the title compound as a white solid m.p. 285°–290° C. (with decomposition).

DESCRIPTION 39

Preparation of 5-chlorobenzofuran-3-carboxylic acid (D39)

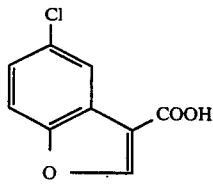

(D39)

The diacid (1.9 g, 0.0079 mole, (D38)) was decarboxylated by the method given in Description 32, to give a grey solid (1.48 g) containing the title compound as the major component.

NMR: δ (CDCl₃/CD₃OD) 4.4 (br.s), 7.1–7.6 (m, 2H), 7.9–8.1 (m, 1H), 8.27 (s, 1H).

DESCRIPTION 40

Preparation of methyl 5-chlorobenzofuran-3-carboxylate (D40)

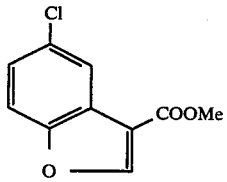

(D40)

The crude acid (1.48 g, assume 0.0075 mole, (D39)) was esterified by the method given in Description 17 to give a brown oil. This was purified by column chromatography on silica gel eluting with 20% ether/pentane, and the resulting yellow oil crystallised from ether/pentane to give the title compound as a pale yellow solid (1.04 g, 61% from diacid (D38)) m.p. 74°–76° C.

NMR: δ (CDCl₃) 3.87 (s, 3H), 7.1–7.5 (m, 2H), 7.9–8.1 (m, 1H), 8.20 (s, 1H).

DESCRIPTION 41

Preparation of methyl 5-chloro-2,3-dihydrobenzofuran-3-carboxylate (D41)

(D41)

The benzofuran ester (250 mg, 1.18 mmole, (D40)) was reduced by the method given in Description 18 using five equivalents of magnesium, to give the title compound as a yellow oil (250 mg, 99%).

NMR: δ (CDCl₃) 3.72 (s, 3H), 4.0–5.0 (m, 3H), 6.60 (d, J=8 Hz, 1H), 7.03 (dd, J=8 Hz and 2 Hz, 1H), 7.23 (dd, J=2 Hz, 1H).

EXAMPLE 1

Preparation of ethyl 7-benzoyl-5-bromo-2,3-dihydrobenzofuran-3-carboxylate (E1)

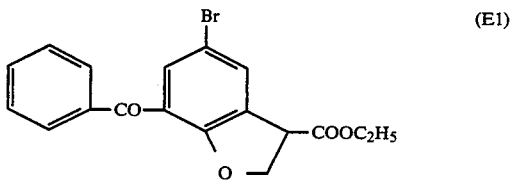

(E1)

A solution of the dihydrobenzofuran ester (2.0 g, 0.0074 mole, (D2)) in carbon disulphide (15 ml) was added to a stirred suspension of benzoyl chloride (5.2 ml, 0.044 mole) and powdered aluminium chloride (4.9 g, 0.037 mole) in carbon disulphide (20 ml) at 0° C. The mixture was stirred at room temperature for 72 hours and then poured onto ice/water (200 ml). The product was extracted with ether (2×150 ml) and the organic solution then washed successively with aqueous 3-dimethylaminopropylamine solution (2×100 ml), 10% sodium carbonate solution (2×100 ml), 1N hydrochloric acid (2×100 ml) and water (2×100 ml); then dried (Na₂SO₄) and evaporated to dryness to leave an orange oil. This was chromatographed on silica gel eluting with 20% ether/pentane to give the title compound as a pale yellow oil (53% of converted material), which was crystallised from ether/pentane, m.p. 100°–101° C.

NMR: δ (CDCl₃) 1.32 (t,J=7 Hz,3H), 4.22 (q,J=7 Hz,2H, 4.1–5.1 (m,3H), 7.2–8.0 (m,7H).

IR: (film)(cm⁻¹) 1660, 1740.

MS: calculated mass for C₁₈H₁₅BrO₄=374.0154. Observed mass=374.0152.

| Analysis | | Calculated | Found |
|---|---|---|---|
| C₁₈H₁₅BrO₄ | C | 57.50 | 57.70 |
| | H | 4.00 | 3.90 |

EXAMPLE 2

Preparation of ethyl 7-benzoyl-2,3-dihydrobenzofuran-3-carboxylate (E2)

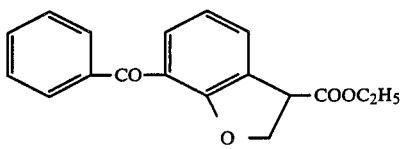
(E2)

A solution of the bromo compound (280 mg, 0.75 mmole, (E1)) in ethyl acetate (30 ml) was added to a suspension of 10% Pd/C (50 mg) and anhydrous potassium acetate (240 mg, 2.4 mmole) in ethyl acetate (20 ml). The mixture was shaken under an atmosphere of hydrogen for 3½ hours and the solid then removed by filtration through kieselguhr. The filtrate was washed with water (2×50 ml), dried ($Na_2SO_4$) and evaporated to dryness to give a yellow oil. This material was purified by chromatography on silica gel, eluting with 30% ether/pentane, to give the title compound as a colourless oil (200 mg, 90%), which was crystallised from ether, m.p. 42°–43° C.

NMR: δ ($CDCl_3$) 1.30 (t,J=7 Hz,3 H), 4.19 (q,J=7 Hz,2H), 4.1–5.1 (m,3H), 6.6–7.9 (m,8H).

IR: (film)(cm$^{-1}$)1660, 1740.

MS: Calculated mass for $C_{18}H_{16}O_4$=296.1049. Observed mass=296.1045.

EXAMPLE 3

Preparation of 7-benzoyl-2,3-dihydrobenzofuran-3-carboxylic acid (E3)

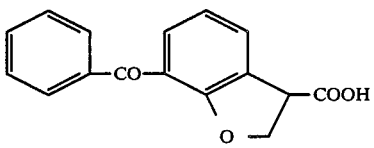
(E3)

A solution of the ethyl ester (200 mg, 0.67 mmole, (E2)) in ethanol (20 ml) was treated with 0.5M sodium hydroxide solution (30 ml) and the resulting mixture stirred at room temperature for 30 minutes. The solution was concentrated to about half of its volume, washed with ether (2×15 ml) and then acidified with 5N hydrochloric acid. The acidic mixture was extracted with ethyl acetate (2×50 ml) and the organic solution then washed with water (2×50 ml) and brine (1×50 ml), dried ($Na_2SO_4$) and evaporated to dryness to leave a colourless oil, which was crystallised from ether to give the title comound as a white solid (150 mg, 82%) m.p. 163°–165°.

NMR: δ ($CDCl_3$) 4.1–5.0 (m,3H), 6.6–7.9 (m,8H), 7.9 (br.s, 1H).

MS: Calculated mass for $C_{16}H_{12}O_4$=268.0736. Observed mass=268.0725.

| Analysis | | Calculated | Found |
|---|---|---|---|
| $C_{16}H_{12}O_4$ | C | 71.65 | 71.40 |
| | H | 4.50 | 4.40 |

EXAMPLE 4

Preparation of 7-benzoyl-5-bromo-2,3-dihydrobenzofuran-3-carboxylic acid (E4)

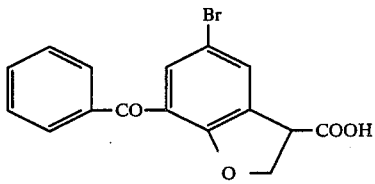
(E4)

The title compound was prepared from the ethyl ester (320 mg, 0.85 mmole, (E1)) by the method given in Example 3, as a white solid (75%) m.p. 173°–175°.

NMR: δ ($CDCl_3$) 4.2–5.1 (m,3H). 7.2–7.9 (m, 7H), 8.3 (br.s, 1H).

MS: Calculated mass for $C_{16}H_{11}BrO_4$=345.9841. Observed mass=345.9838.

| Analysis | | Calculated | Found |
|---|---|---|---|
| $C_{16}H_{11}BrO_4$ | C | 55.30 | 54.95 |
| | H | 3.15 | 3.10 |

EXAMPLE 5

Preparation of ethyl 7-benzoyl-5-chloro-2,3-dihydrobenzofuran-3-carboxylate (E5)

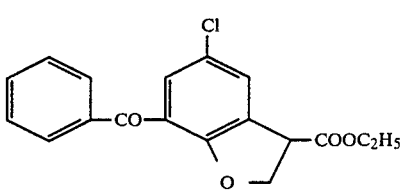
(E5)

The title compound was prepared from the dihydrobenzofuran ester (660 mg, 2.9 mmole, (D4)) by the method given in Example 1, as a yellow solid (420 mg, 44%) m.p. 90°–91°.

NMR: δ ($CDCl_3$) 1.30(t,J=7 Hz,3H), 4.21 (q,J=7 Hz,2H), 4.2–5.1 (m,3H), 7.2–7.9 (m,7H).

IR: ($CCl_4$)(cm$^{-1}$) 1660, 1740.

UV: λmax (EtOH) (nm) 253, 332.

MS: Calculated mass for $C_{18}H_{15}ClO_4$=330.0658. Observed mass=330.0667.

| Analysis | | Calculated | Found |
|---|---|---|---|
| $C_{18}H_{15}ClO_4$ | C | 65.35 | 65.25 |
| | H | 4.55 | 4.65 |
| | Cl | 10.75 | 10.85 |

EXAMPLE 6

Preparation of 7-Benzoyl-5-chloro-2,3-dihydrobenzofuran-3-carboxylic acid (E6)

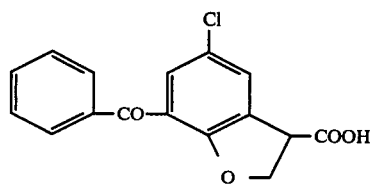

(E6)

The title compound was prepared from the ethyl ester (115 mg, 0.35 mmole, (E5)) by the method given in Example 3, as a white solid (82 mg) 77%). M.p. 155°–157°.

NMR: δ (CDCl$_3$) 4.1–5.0 (m,3H), 7.1–7.8 (m,7H), 10.13 (br.s,1H).

| Analysis | | Calculated | Found |
|---|---|---|---|
| C$_{16}$H$_{11}$ClO$_4$ | C | 63.50 | 63.55 |
| | H | 3.65 | 3.60 |
| | Cl | 11.75 | 11.75 |

EXAMPLE 7

Preparation of 6-benzoyl-2.7-dihydroisobenzofuran-2-carboxylic acid (E7)

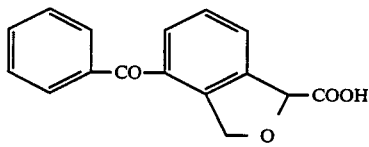

(E7)

The entire product from Description 10 was treated with concentrated hydrochloric acid (5 ml) under nitrogen. After stirring for half an hour at room temperature, the mixture was heated to 80° for one hour. The slurry so formed was cooled to room temperature and partitioned between 5% sodium hydrogen carbonate solution (40 ml) and ethyl acetate (50 ml). Further solid sodium hydrogen carbonate was added until effervescence ceased. The organic layer was discarded and the aqueous solution was made acidic with 5M hydrochloric acid (to pH2). The solid so precipitated was extracted with ethyl acetate (2×100 ml) and chloroform (300 ml). The combined extracts were washed with brine (30 ml) and dried over sodium sulphate. Removal of the solvent under reduced pressure gave 6-benzoyl-2.7-dihydroisobenzofuran-2-carboxylic acid (104 mg), with m.p. 182°–4° C. (Ether).

NMR: δ (CD$_3$OD) 5.46 (m,2H), 5.73 (m,1H), 7.35–7.9 (m,8H).

IR: (nujol mull) (cm$^{-1}$) 1650, 1715.

HRMS: C$_{16}$H$_{12}$O$_{14}$ requires 268.0736, found 268.0722.

EXAMPLE 8

Preparation of ethyl 7-(2-thienoyl)-5-chloro-2,3-dihydrobenzofuran-3-carboxylate (E8)

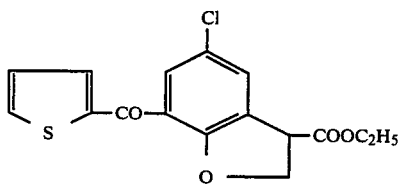

(E8)

The title compound was prepared from the dihydrobenzofuran ester (4.0 g, 17.7 mmole, (D4)) by a method analogous to that given in Example 1, by substituting 2-thienoyl chloride for benzoyl chloride. The product was obtained as a yellow oil (770 mg, 13%).

NMR: δ (CDCl$_3$) 1.30 (t, J=7 Hz, 3H), 4.21 (q, J=7H, 2H), 4.2–5.0 (m, 3H), 6.9–7.7 (m, 5H).

EXAMPLE 9

Preparation of 7-(2'-thienoyl)-5-chloro-2,3-dihydrobenzofuran-3-carboxylic acid (E9)

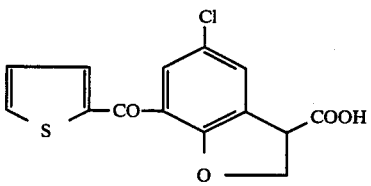

(E9)

The title compound was prepared from the ethyl ester (750 mg, 2.2 mmole, (E 8)) by the method given in Example 3, as a white solid (270 mg, 40%). M.p. 130°–132°.

NMR: δ (CDCl$_3$) 4.3–5.2 (m, 3H), 7.1–7.9 (m, 5H), 8.7 (br.s, 1H).

MS: Calculated mass for C$_{14}$H$_9$ClO$_4$S=307.9910. Observed mass=307.9908.

| Analysis | | Calculated | Found |
|---|---|---|---|
| C$_{14}$H$_9$ClO$_4$S | C | 54.45 | 54.40 |
| | H | 2.95 | 2.90 |
| | Cl | 11.50 | 11.40 |

EXAMPLE 10

Preparation of ethyl 7-(4-chlorobenzoyl)-5-chloro-2,3-dihydrobenzofuran-3-carboxylate (E10)

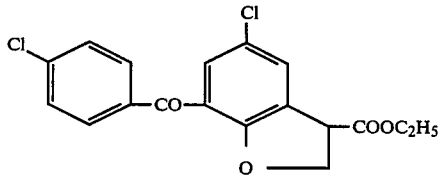

(E10)

The title compound was prepared from the dihydrobenzofuran ester (1.25 g, 5.5 mmole, (D4)) by a method analogous to that given in Example 1, by substituting 4-chlorobenzoyl chloride for benzoyl chloride. The product was obtained as a yellow oil (44% of converted material).

NMR: δ (CDCl$_3$) 1.30 (t, J=7 Hz, 3H), 4.14 (q, J=7 Hz, 2H), 4.2–5.0 (m, 3H), 7.1–7.7 (m, 6H).

EXAMPLE 11

Preparation of 7-(4'-chlorobenzoyl)-5-chloro-2,3-dihydrobenzofuran-3-carboxylic acid (E11)

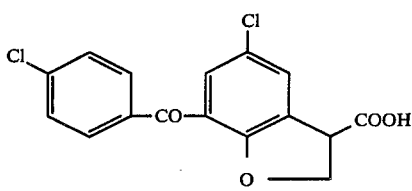

(E11)

The title compound was prepared from the ethyl ester (190 mg, 0.52 mmole, (E 10)) by the method given in Example 3, as a pale yellow solid (107 mg, 61%). M.p. 161°–163°.

NMR: δ (CDCl$_3$) 4.2–5.1 (m, 3H), 7.2–7.9 (m, 6H).

MS: Calculated mass for C$_{16}$H$_{10}$Cl$_2$O$_4$=335.9955. Observed mass=335.9953.

| Analysis | | Calculated | Found |
|---|---|---|---|
| C$_{16}$H$_{10}$Cl$_2$O$_4$ | C | 56.95 | 56.70 |
| | H | 2.95 | 2.95 |

EXAMPLE 12

Preparation of ethyl 7-benzoyl-5-fluoro-2,3-dihydrobenzofuran-3-carboxylate (E12)

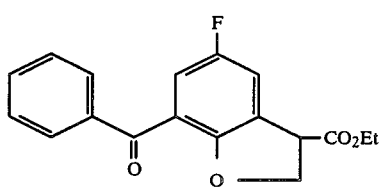

(E12)

The title compound was prepared from the dihydrobenzofuran ester (1.82 g, 0.0087 mole, (D14)) by the method given in Example 1, as a colourless oil (0.313 g, 12%) after purification by hydrolysis and re-esterification followed by chromatography on silica gel eluting with 25% ether/pentane.

NMR: δ (CDCl$_3$) 1.3 (t, J=7 Hz, 3H), 3.9–5.0 (m, 5H), 6.8–7.8 (m, 7H).

EXAMPLE 13

Preparation of 7-benzoyl-5-fluoro-2,3-dihydrobenzofuran-3-carboxylate (E13)

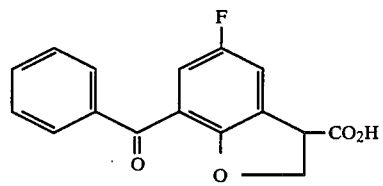

(E13)

The title compound was prepared from the ethyl ester (205 mg, 0.65 mmole, (E12)) by method given in Example 3, as a pale yellow solid (88 mg, 47%) after recrystallisation from carbon tetrachloride.

M.p. 135°–137°.

NMR: δ (CDCl$_3$) 4.25–5.75 (m, 4H, including br.s at 5.25), 7.0–8.0 (m, 7H).

MS: Calculated mass for C$_{16}$H$_{11}$FO$_4$=286.0641. Observed mass=286.0641.

EXAMPLE 14

Preparation of ethyl 7-benzoyl-5-bromo-2,3-dihydrobenzothiophene-3-carboxylate (E14)

(E14)

A solution of the dihydrobenzothiophene ester (2.2 g, 0.0077 mole, (D20)) in carbon disulphide (15 ml) was added to a stirred suspension of benzoyl chloride (5.4 ml, 0.046 mole) and powdered aluminium chloride (5.14 g, 0.038 mole) in carbon disulphide (50 ml). The mixture was stirred at room temperature for 9 days and then poured onto ice/water (300 ml). The product was extracted with ethyl acetate (2×200 ml) and the organic solution was washed successively with aqueous 3-dimethylaminopropylamine solution (2×150 ml), 10% sodium carbonate solution (2×150 ml), 1M hydrochloric acid (2×150 ml) and water (2×150 ml); then dried (MgSO$_4$) and evaporated to dryness to leave an orange oil. This was chromatographed on a silica gel column eluting with 20% ether/pentane to remove starting material and base-line components. The fractions containing required product were then combined and purified on a silica gel chromatotron plate eluting with toluene. The title compound was isolated as a yellow oil (250 mg, 8%).

NMR: δ (CDCl$_3$) 1.30 (t, J=7 Hz, 3H), 3.2–3.9 (m, 2H), 4.1–4.5 (m, 1H), 4.22 (q, J=7 Hz, 2H), 7.2–7.8 (m, 7H).

IR: (film)(cm$^{-1}$) 1650, 1735.

EXAMPLE 15

Preparation of ethyl 7-benzoyl-2,3-dihydrobenzothiophene-3-carboxylate (E15)

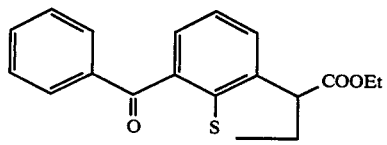
(E15)

A solution of the bromo ester (250 mg, 0.64 mmole, (E14)) in ethyl acetate (20 ml) was added to a suspension of 10% Pd/C (50 mg) and anhydrous sodium acetate (200 mg) in ethyl acetate (30 ml). The mixture was shaken under an atmosphere of hydrogen for 50 hours and the solid then removed by filtration through kieselguhr. The filtrate was evaporated to dryness to leave a yellow oil which was purified on a silica gel chromatotron plate eluting with toluene. The title compound was isolated as a yellow oil (135 mg, 68%).

NMR: δ (CDCl$_3$) 1.28 (t, J=7 Hz, 3H), 3.2–3.9 (m, 2H), 4.1–4.5 (m, 1H), 4.17 (q, J=7 Hz, 2H), 6.8–7.2 (m, 1H), 7.2–7.8 (m, 7H).

IR: (film)(cm$^{-1}$) 1650, 1735.

EXAMPLE 16

Preparation of 7-benzoyl-2,3-dihydrobenzothiophene-3-carboxylic acid (E16)

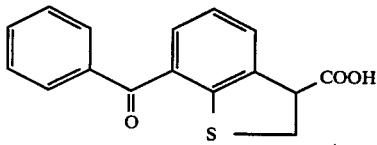
(E16)

A solution of the ethyl ester (170 mg, 0.54 mmole, (E15) in ethanol (50 ml) was stirred together with 1% sodium carbonate solution (50 ml) at room temperature for 1½ hours. The solution was acidified with dilute hydrochloric acid, concentrated to about half its volume and then extracted with ether (2×60 ml). The ether solutions were combined and extracted with 10% sodium carbonate solution (2×50 ml). The basic extracts were then acidified with dilute hydrochloric acid and extracted with ether (2×60 ml). The ether extracts were combined, washed with water, dried (MgSO$_4$) and then evaporated to dryness to give a pale yellow oil (118 mg, 77%). This was crystallised from ether/pentane to give the title compound as a pale yellow solid m.p. 153°–156°.

NMR: δ (CDCl$_3$) 3.3–3.9 (m, 2H), 4.2–4.6 (m, 1H), 6.9–7.3 (m, 1H), 7.3–7.8 (m, 7H), 9.9–10.3 (br.s, 1H).

| Analysis | | Calculated | Found |
|---|---|---|---|
| C$_{16}$H$_{12}$O$_3$S | C | 67.60% | 67.50% |
| | H | 4.25% | 4.20% |

EXAMPLE 17

Preparation of 7-benzoyl-5-bromo-2,3-dihydrobenzothiophene-3-carboxylic acid (E17)

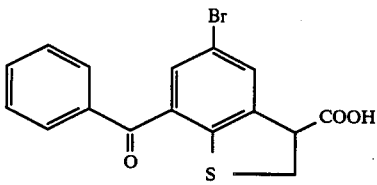
(E17)

The title compound was prepared from the ethyl ester (250 mg, 0.64 mmole, (E14)) by the method given in Example 16, yielding a yellow oil (170 mg, 73%), which crystallised from ether/pentane as a pale yellow solid m.p. 192°–194° C.

NMR: δ (CDCl$_3$) 3.45–3.60 (m, 1H), 3.70–3.80 (m, 1H), 4.35–4.50 (m, 1H), 7.45–7.85 (m, 7H).

| Analysis | | Calculated | Found |
|---|---|---|---|
| C$_{16}$H$_{11}$BrO$_3$S | C | 52.90 | 52.75% |
| | H | 3.05 | 3.00% |

EXAMPLE 18

Preparation of ethyl 7-benzoyl-5-chloro-2,3-dihydrobenzothiophene-3-carboxylate (E18)

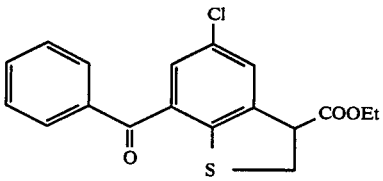
(E18)

The dihydrobenzothiophene ester (4.85 g, 0.02 mole, (D27)) was benzoylated using the method given in Example 14, with the exceptions that the reaction mixture was stirred at room temperature for seven days before working-up and that the crude product only required purification by silica gel column to yield starting material (2.5 g) and the title compound as a yellow oil (2.66 g, 79% of converted material).

NMR: δ (CDCl$_3$) 1.30 (t, J=7 Hz, 3H), 3.2–3.9 (m, 2H), 4.1–4.5 (m, 1H), 4.17 (q, J=7 Hz, 2H), 7.2–7.7 (m, 7H).

IR: (film) (cm$^{-1}$) 1650, 1735.

EXAMPLE 19

Preparation of 7-benzoyl-5-chloro-2,3-dihydrobenzothiophene-3-carboxylic acid (E19)

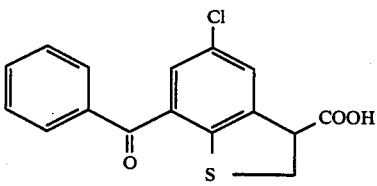
(E19)

The title compound was prepared from the ethyl ester (550 mg, 1.59 mmole, (E18) by the method given in Example 16, yielding a yellow oil which crystallised from carbon tetrachloride as a pale yellow solid (340 mg, 67%) m.p. 177°–179° C.

NMR: δ (CDCl₃) 3.2–3.9 (m, 2H), 4.1–4.5 (m, 1H), 7.2–7.7 (m, 7H), 9.2–9.6 (br.s, 1H).

| Analysis | | Calculated | Found |
|---|---|---|---|
| C₁₆H₁₁O₃SCl | C | 60.30% | 60.65% |
| | H | 3.50% | 3.20% |
| | Cl | 11.15% | 11.25% |

EXAMPLE 20

Preparation of ethyl 7-benzoyl-5-chloro-2,3-dihydro-1-oxo-benzothiophene-3-carboxylate (E20)

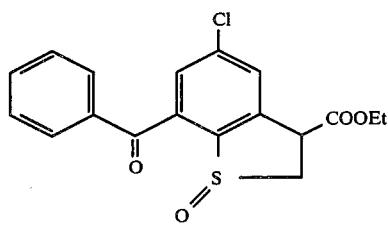

(E20)

A solution of the dihydrobenzothiophene (346 mg, 0.0010 mole, (E18)) in acetone (10 ml) was treated with a solution of sodium periodate (225 mg, 0.0011 mole) in water (10 ml) and the mixture stirred at room temperature for 24 hours. The solution was poured into water (150 ml) and the mixture extracted with ethyl acetate (2×100 ml). The organic solution was washed with brine (2×100 ml), dried (MgSO₄) and evaporated to dryness to leave a pale yellow oil. This was purified on a silica gel column eluting with ethyl acetate, to give the title compound as a colourless oil (350 mg, 97%).

NMR: δ (CDCl₃) 1.32 (t, J=7 Hz, 3H), 3.3–3.8 (m, 2H), 4.22 (q, J=7 Hz, 2H), 4.0–4.4 and 4.7–5.1 (2 multiplets equivalent to 1H), 7.2–7.9 (m, 7H).

IR: (CDCl₃) (cm⁻¹) 1665, 1735.

EXAMPLE 21

Preparation of 7-benzoyl-5-chloro-2,3-dihydro-1-oxobenzothiophene-3-carboxylic acid (E21)

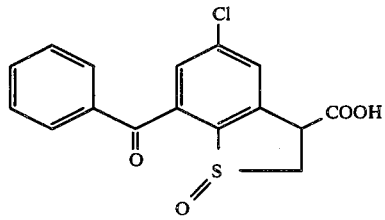

(E21)

The ethyl ester (350 mg, 0.965 mmole, (E20)) was hydrolysed by the method given in Example 16 yielding a pale yellow solid, which was recrystallised from chloroform/pentane to give the title compound as a white solid (120 mg, 37%) m.p. 172°–174° C.

NMR: δ (CD₃OD/CDCl₃) 3.4–3.8 (m, 2H), 3.8–4.0 and 4.9–5.1 (2 multiplets equivalent to 1H), 7.4–8.0 (m, 7H).

EXAMPLE 22

Preparation of ethyl 7-benzoyl-5-chloro-2,3-dihydro-1,1-dioxobenzothiophene-3-carboxylate (E22)

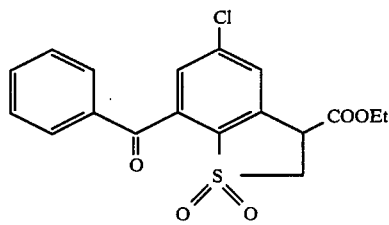

(E22)

A solution of the dihydrobenzothiophene (500 mg, 0.0014 mole, (E18) in dichloromethane (30 ml) was cooled in an ice/water bath and treated portionwise with m-chloroperoxybenzoic acid (660 mg of 80% purity, 0.0031 mole). The resulting mixture was stirred at ice bath temperature for 4 hours and then diluted with chloroform (100 ml). The organic solution was washed with 10% sodium carbonate solution (2×50 ml), dilute hydrochloric acid (1×50 ml) and brine (2×50 ml); then dried (MgSO₄) and evaporated to dryness to give a colourless oil. This was purified on a silica gel column eluting with ether and the resulting colourless oil crystallised from ether/pentane to give the title compound as a white solid (400 mg, 73%) m.p. 138°–139° C.

NMR: δ (CDCl₃) 1.37 (t, J=7 Hz, 3H), 3.6–3.9 (m, 2H), 4.35 (q, J=7 Hz, 2H), 4.2–4.6 (m, 1H), 7.3–8.0 (m, 7H).

IR: (CDCl₃) (cm⁻¹) 1670, 1735.

MS: Calculated mass for C₁₈H₁₅ClO₅S=378.0328. Observed mass=378.0318.

| Analysis | | Calculated | Found |
|---|---|---|---|
| C₁₈H₁₅ClO₅S | C | 57.05% | 57.25% |
| | H | 4.00% | 3.90% |
| | Cl | 9.40% | 9.60% |

EXAMPLE 23

Preparation of 7-benzoyl-5-chloro-2,3-dihydro-1,1-dioxobenzothiophene-3-carboxylic acid (E23)

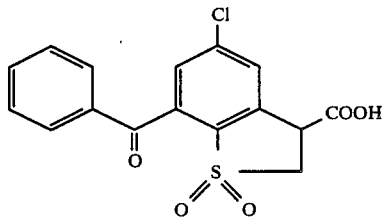

(E23)

The ethyl ester (400 mg, 0.0011 mole, (E22)) was hydrolysed by the method given in Example 16 yielding a white solid, which was recrystallised from ether/pentane to give the title compound as a white solid m.p. 158°–161° C.

NMR: δ (CDCl₃) 3.6–4.1 (m, 2H), 4.4–4.7 (m, 1H), 7.3–7.9 (m, 7H), 8.6 (br.s, 1H).

| Analysis | | Calculated | Found |
|---|---|---|---|
| C₁₆H₁₁O₅SCl | C | 54.80% | 55.30% |
| | H | 3.15% | 3.15% |

EXAMPLE 24

Preparation of methyl 7-benzoyl-5-methyl-2,3-dihydrobenzofuran-3-carboxylate (E24)

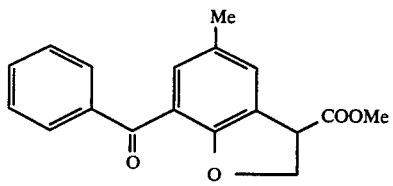

(E24)

A solution of the dihydrobenzofuran ester (1.30 g, 0.0068 mole, (D34)) in carbon disulphide (5 ml) was added to a stirred suspension of benzoyl chloride (3.1 ml, 0.027 mole) and powdered aluminium chloride (2.7 g, 0.020 mole) in carbon disulphide (25 ml). The mixture was stirred at room temperature for 1½ hours and then poured into ice/dilute hydrochloric acid (400 ml). The product was extracted with ethyl acetate (2×200 ml) and the organic solution then washed successively with aqueous 3,3-dimethylaminopropylamine solution (2×150 ml), dilute hydrochloric acid (2×150 ml) and water (2×150 ml); then dried (MgSO₄) and evaporated to dryness to leave a red oil. This was purified on a silica gel column eluting with 30% ether/pentane, and the resulting pale yellow solid was recrystallised from ether/pentane to give the title compound as a white solid (1.10 g, 55%) m.p. 110°–111° C.

NMR: δ (CDCl₃) 2.27 (s, 3H), 3.70 (s, 3H), 4.0–4.9 (m, 3H), 7.0–7.8 (m, 7H).

EXAMPLE 25

Preparation of 7-benzoyl-5-methyl-2,3-dihydrobenzofuran-3-carboxylic acid (E25)

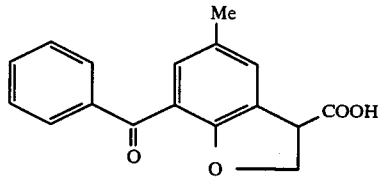

(E25)

The title compound was prepared from the methyl ester (800 mg, 0.0027 mole, (E24)) by the method given in Example 16 yielding a yellow gum, which crystallised from ether/pentane as an off-white solid (525 mg, 69%) m.p. 161°–163° C.

NMR: δ (CDCl₃) 2.32 (s, 3H), 4.2–5.0 (m, 3H), 7.2–7.9 (m, 7H), 10.7 (br.s, 1H).

| Analysis | | Calculated | Found |
|---|---|---|---|
| C₁₇H₁₄O₄ | C | 72.35% | 72.60% |
| | H | 5.00% | 5.00% |

PHARMACOLOGICAL DATA

The compounds of the Examples 3 and 6 were examined for analgesic activity in the conventional phenylquinone induced writhing test in mice (J. Pharm. Exp. Therap., 125, 237–240 (1959)).

| Analgesic Phenylquinone Writhing Test | | |
|---|---|---|
| Compound of Example No. | Dose mgkg⁻¹ (po) | % of Animals exhibiting Analgesia |
| 3 | 5 | 90% |
| | 1 | 60% |
| 6 | 5 | 100% |
| | 1 | 60% |

The compounds of Examples 3 and 6 were also examined for gastric irritancy in rats (J. Pharm. Pharmacol., 28, 865–868 (1976)). Both compounds showed no gastric irritation at doses of 5, 15 or 45 mg kg⁻¹ (po).

What we claim is:

1. A compound of formula (I):

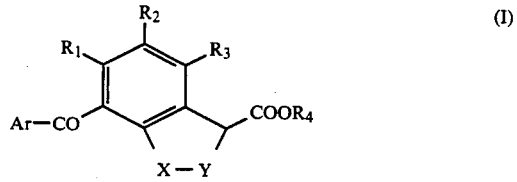

(I)

wherein:
Ar is phenyl optionally substituted in the o-, m- or p-position by $C_{1-4}$ alkyl, $C_{1-4}$ alkoxy, trifluoromethyl, bromo, chloro or fluoro,
pyrryl optionally N-substituted by $C_{1-4}$ alkyl,
2-furyl or 2-thienyl either optionally substituted in the 3-, 4- or 5-position by methyl, chloro or bromo, or
3-furyl or 3-thienyl;
X is oxygen, sulphur, sulphoxide or sulphone, Y is methylene, $R_1$ and $R_3$ are hydrogen or $C_{1-4}$ alkyl, and $R_2$ is hydrogen, $C_{1-4}$ alkyl, fluoro, chloro or bromo, or X is methylene, Y is oxygen, $R_1$ and $R_3$ are both hydrogen, and $R_2$ is hydrogen, fluoro, chloro or bromo; and
$R_4$ is hydrogen or $C_{1-4}$ alkyl, or a salt thereof.

2. A compound according to claim 1, wherein Ar is phenyl optionally substituted in the the o-, m- or p-position by $C_{1-4}$ alkyl, $C_{1-4}$ alkoxy, trifluoromethyl, bromo, chloro or fluoro.

3. A compound according to claim 1, wherein Ar is unsubstituted phenyl or p-chlorophenyl.

4. A compound according to claim 1, wherein X is oxygen and Y is methylene.

5. A compound according to claim 1, wherein X is sulphur, sulphoxide or sulphone and Y is methylene.

6. A compound according to claim 1, wherein X is methylene and Y is oxygen.

7. A compound according to claim 1, wherein $R_1$ and $R_3$ are hydrogen.

8. A compound according to claim 1, wherein $R_2$ is hydrogen, fluoro or chloro.

9. A compound according to claim 1, wherein $R_4$ is hydrogen.

10. 7-Benzoyl-2,3-dihydrobenzofuran-3-carboxylic acid; 7-benzoyl-5-fluoro-2,3-dihydrobenzofuran-3-carboxylic acid; 7-benzoyl-5-chloro-2,3-dihydrobenzofuran-3-carboxylic acid; 7-benzoyl-2,3-dihydrobenzothiophene-3-carboxylic acid; and 7-benzoyl-5-chloro-2,3-dihydrobenzothiophene-3-carboxylic acid; or a pharmaceutically acceptable salt thereof.

11. Ethyl 7-benzoyl-5-bromo-2,3-dihydrobenzofuran-3-carboxylate; ethyl 7-benzoyl-2,3-dihydrobenzofuran-3-carboxylate; 7-benzoyl-5-bromo-2,3-dihydrobenzofuran-3-carboxylic acid; ethyl 7-benzoyl-5-chloro-2,3-dihydrobenzofuran-3-carboxylate; 6-benzoyl-2,7-dihydroisobenzofuran-2-carboxylic acid; ethyl 7-(2-thienoyl)-5-chloro-2,3-dihydrobenzofuran-3-carboxylate; 7-(2-thienoyl)-5-chloro-2,3-dihydrobenzofuran-3-carboxylic acid; ethyl 7-(4-chlorobenzoyl)-5-chloro-2,3-dihydrobenzofuran-3-carboxylate; 7-(4-chlorobenzoyl)-5-chloro-2,3-dihydrobenzofuran-3-carboxylic acid; ethyl 7-benzoyl-5-fluoro-2,3-dihydrobenzofuran-3-carboxylate; ethyl 7-benzoyl-5-bromo-2,3-dihydrobenzothiophene-3-carboxylate; ethyl 7-benzoyl-2,3-dihydrobenzothiophene-3-carboxylate; 7-benzoyl-5-bromo-2,3-dihydrobenzo-thiophene-3-carboxylic acid; ethyl 7-benzoyl-5-chloro-2,3-dihydrobenzothiophene-3-carboxylate; ethyl 7-benzoyl-5-chloro-2,3-dihydro-1-oxobenzothiophene-3-carboxylate; 7-benzoyl-5-chloro-2,3-dihydro-1-oxobenzothiophene-3-carboxylic acid; ethyl 7-benzoyl-5-chloro-2,3-dihydro-1,1-dioxobenzothiophene-3-carboxylate; 7-benzoyl-5-chloro-2,3-dihydro-1,1-dioxobenzothiophene-3-carboxylic acid; methyl-7-benzoyl-5-methyl-2,3-dihydrobenzofuran-3-carboxylate; 7-benzoyl-5-methyl-2,3-dihydrobenzofuran-3-carboxylic acid; or a pharmaceutically acceptable salt thereof.

12. An anti-inflammatory composition, which comprises an anti-inflammatory effective amount of a compound according to claim 1, or a pharmaceutically acceptable salt thereof, and a pharmaceutically acceptable carrier.

13. A method of treating a painful and/or inflammatory condition in a mammal which comprises administering an analgesic or anti-inflammatory effective amount of a compound, according to claim 1, or a pharmaceutically acceptable salt thereof, to the mammal.

* * * * *